US009326939B2

(12) United States Patent
Paulson et al.

(10) Patent No.: US 9,326,939 B2
(45) Date of Patent: May 3, 2016

(54) LIPOSOME TARGETING COMPOUNDS AND RELATED USES

(75) Inventors: James C. Paulson, Del Mar, CA (US);
Weihsu Claire Chen, Toronto (CA);
Norihito Kawasaki, San Diego, CA (US); Corwin Nycholat, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 44 days.

(21) Appl. No.: 13/261,581

(22) PCT Filed: Jul. 29, 2011

(86) PCT No.: PCT/US2011/001339
§ 371 (c)(1),
(2), (4) Date: Feb. 28, 2013

(87) PCT Pub. No.: WO2012/018377
PCT Pub. Date: Feb. 9, 2012

(65) Prior Publication Data
US 2013/0164364 A1 Jun. 27, 2013

Related U.S. Application Data

(60) Provisional application No. 61/400,610, filed on Jul. 31, 2010.

(51) Int. Cl.
| A61K 9/127 | (2006.01) |
| A61K 39/00 | (2006.01) |
| A61K 31/715 | (2006.01) |
| A61K 49/00 | (2006.01) |

(52) U.S. Cl.
CPC .............. *A61K 9/1271* (2013.01); *A61K 9/127* (2013.01); *A61K 31/715* (2013.01); *A61K 39/00* (2013.01); *A61K 49/0084* (2013.01)

(58) Field of Classification Search
CPC ... A61K 9/1271; A61K 31/715; A61K 39/00; A61K 49/0084; A61K 49/0052
See application file for complete search history.

(56) References Cited

U.S. PATENT DOCUMENTS

| 8,357,671 B2 * | 1/2013 | Paulson et al. ................. 514/53 |
| 2001/0031262 A1 | 10/2001 | Caplan et al. |
| 2009/0186073 A1 | 7/2009 | Yamazaki et al. |
| 2010/0129392 A1 | 5/2010 | Shi et al. |

FOREIGN PATENT DOCUMENTS

| WO | WO-2007/056525 A2 | 5/2007 |
| WO | WO-2012/018377 A2 | 2/2012 |
| WO | WO-2012/018377 A3 | 2/2012 |

OTHER PUBLICATIONS

Tupin and Kronenberg (2006) "Activation of Natural Killer T Cells by Glycolipids", Methods in Enzymology, 417: 185-201, pp. 186-187.*
"European Application Serial No. 11814895.6, Extended European Search Report mailed Apr. 7, 2014", 11 pgs.
"European Application Serial No. 11814895.6, Office Action mailed Jul. 2, 2013", 2 pgs.
"European Application Serial No. 11814895.6, Response filed Nov. 7, 2014 to Extended European Search Report mailed Apr. 7, 2014", 14 pgs.
"International Application Serial No. PCT/US2011/001339, International Preliminary Report on Patentability mailed Feb. 14, 2013", 7 pgs.
"International Application Serial No. PCT/US2011/001339, International Search Report mailed Mar. 16, 2012", 5 pgs.
"International Application Serial No. PCT/US2011/001339, Written Opinion mailed Mar. 16, 2012", 6 pgs.
Chen, Weihsu C, et al., "Antigen Delivery to Macrophages Using Liposomal Nanoparticles Targeting Sialoadhesin/CD169", *PLoS ONE*, 7(6), e39039, (2012), 1-9.
Chen, Weihsu C., et al., "In vivo targeting of B-cell lymphoma with glycan ligands of CD22", *Blood*, 115(23), (2010), 4778-4786.
Copland, Melissa J., et al., "Liposomal delivery of antigen to human dendritic cells", *Vaccine*, 21, (2003), 883-890.
Duong, Bao H., et al., "Decoration of T-independent antigen with ligands for CD22 and Siglec-G can suppress immunity and induce B cell tolerance in vivo", *Journal of Experimental Medicine*, 207(1), (2010), 173-187.
Huan, Anthony, et al., "Interactions of Immunoliposomes with Target Cells", *The Journal of Biological Chemistry*, 258(22), (1983), 14034-14040.
Kawasaki, Norihito, et al., "Targeted delivery of lipid antigen to macrophages via the CD169/sialoadhesin endocytic pathway induces robust invariant natural killer T cell activation", *Proc. Natl. Acad. Sci. USA*, 110(19), (May 2013), 7826-7831.

(Continued)

*Primary Examiner* — Robert M Kelly
(74) *Attorney, Agent, or Firm* — Schwegman Lundberg & Woessner, P.A.

(57) ABSTRACT

The present invention provides liposome targeting compounds for targeting cells expressing sialic acid binding Ig-like lectin (Siglec). The liposome compounds typically comprise a binding moiety that is a glycan ligand of the Siglec on the target cell. The liposome compounds also incorporate or encapsulate a biological agent (e.g., an antigen or a therapeutic agent) that can be delivered to the target cell to modulate or kill the target cell. The invention also provides methods of using the liposome targeting compounds for targeted delivery of antigen and for modulating immune cells or immune responses.

7 Claims, 17 Drawing Sheets

(56) References Cited

OTHER PUBLICATIONS

Kreitman, Robert J., et al., "Cytotoxic Activity of Disulfide-stabilized Recombinant Immunotoxin RFB4(dsFv)-PE38 (BL22) toward Fresh Malignant Cells from Patients with B-Cell Leukemias", *Clin. Cancer Res.*, 6(4), (2000), 1476-1487.

Lanoue, Astrid, et al., "Interaction of CD22 with α2,6-linked sialoglycoconjugates: innate recognition of self to dampen B cell autoreactivity?", *European Journal of Immunology*, 32(2), (2002), 348-355.

Loomis, K, et al., "Specific targeting to B cells by lipid-based nanoparticles conjugated with a novel CD22-ScFv", *Author Manuscript, published in final edited form in Experimental and Molecular Pathology*, 88(2), 238-249, (2010), 33 pgs.

Macauley, Matthew S., et al., "Antigenic liposomes displaying CD22 ligands induce antigen-specific B cell apoptosis", *Journal of Clinical Investigations*, 123(7), (2013), 3074-3083.

O'Reilly, Mary K., et al., "Siglecs as targets for therapy in immune-cell-mediated disease", *Trends in Pharmacological Sciences*, 30(5), (2009), 240-248.

Pfrengle, Fabian, et al., "Copresentation of Antigen and Ligands of Siglec-G Induces B Cell Tolerance Independent of CD22", *Journal of Immunology*, 191(4), (Aug. 2013), 1724-1731.

Van Broekhoven, Christina L., et al., "Targeting Dendritic Cells with Antigen-Containing Liposomes: A Highly Effective Procedure for induction of Antitumor Immunity and for Tumor Immunotherapy", *Cancer Research*, 64(12), (2004), 4357-4365.

European Application Serial No. 11814895.6, Office Action mailed Dec. 18, 2015, 8 pgs.

\* cited by examiner

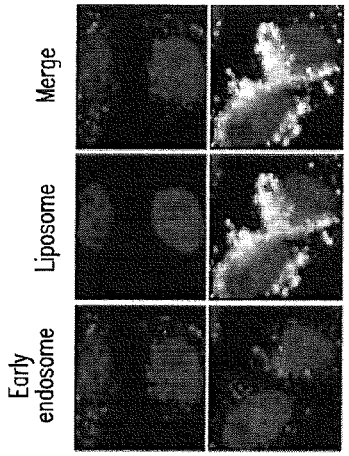
FIG. 2A
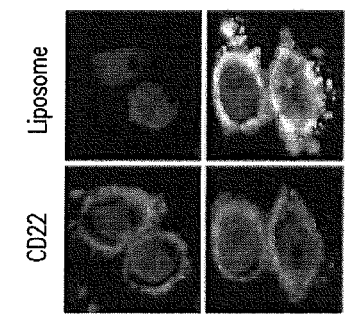
FIG. 2D
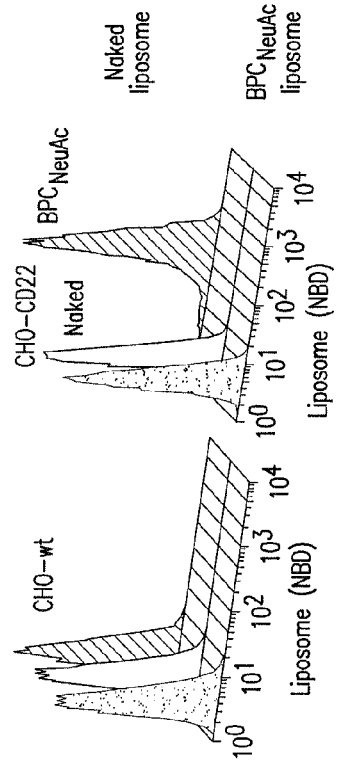
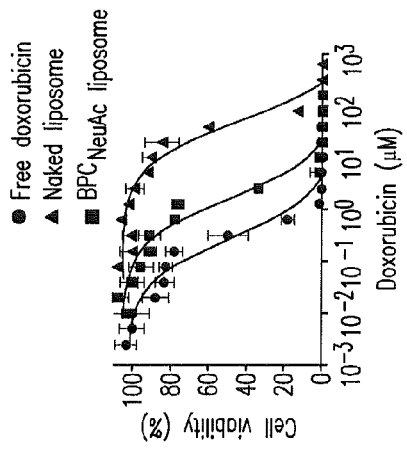
FIG. 2B
FIG. 2C
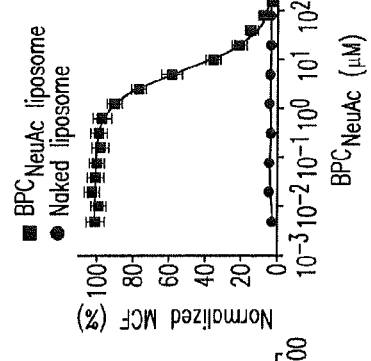
FIG. 2E
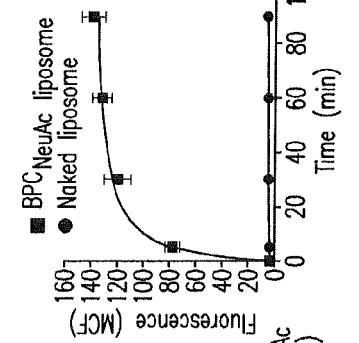
FIG. 2F
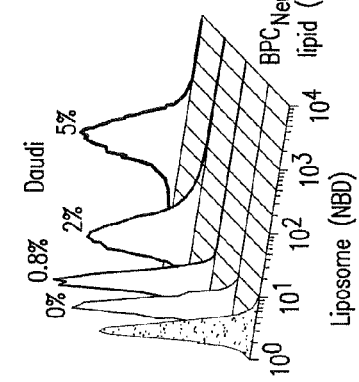
FIG. 2G

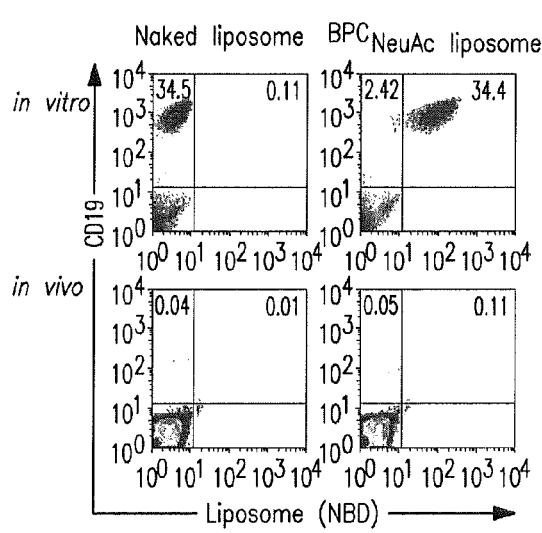
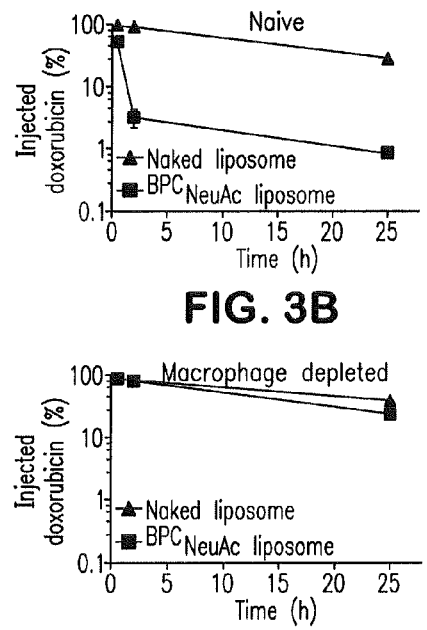
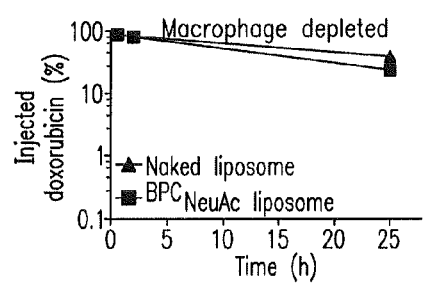
FIG. 3A
FIG. 3B
FIG. 3C
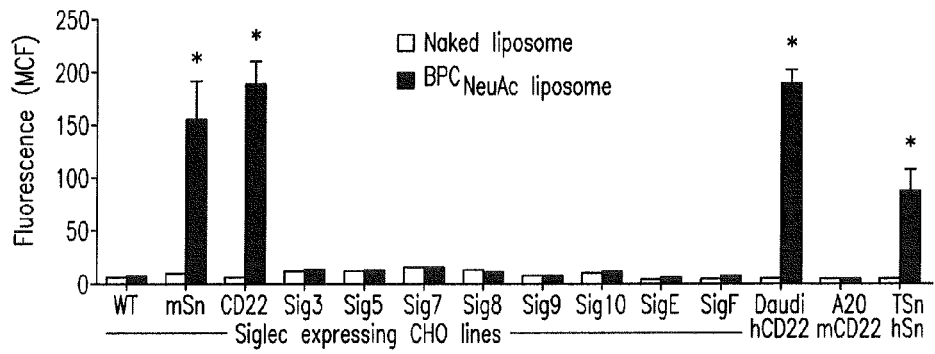
FIG. 3D
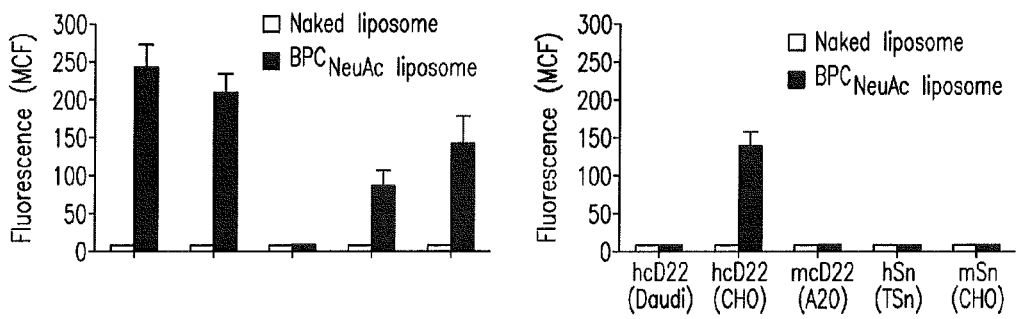
FIG. 3E

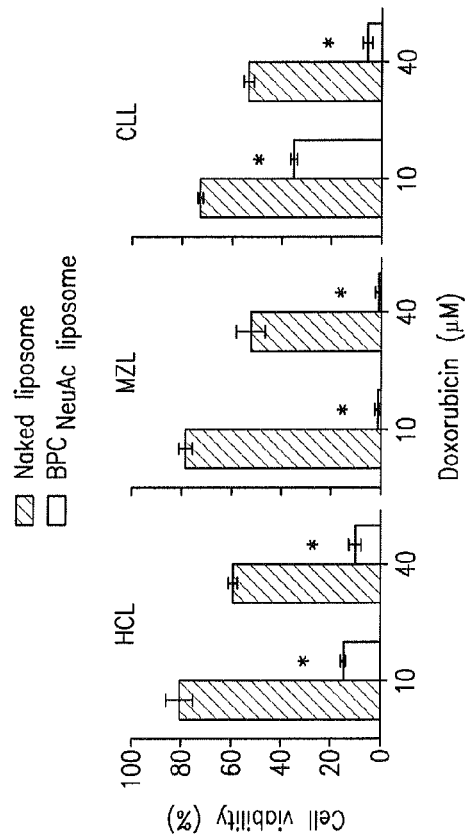
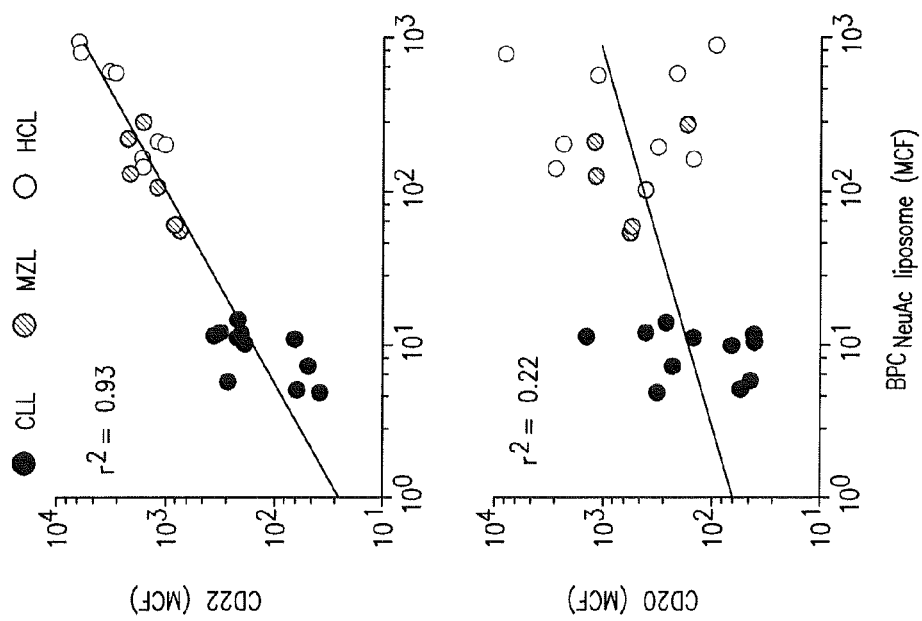
FIG. 5A
FIG. 5B

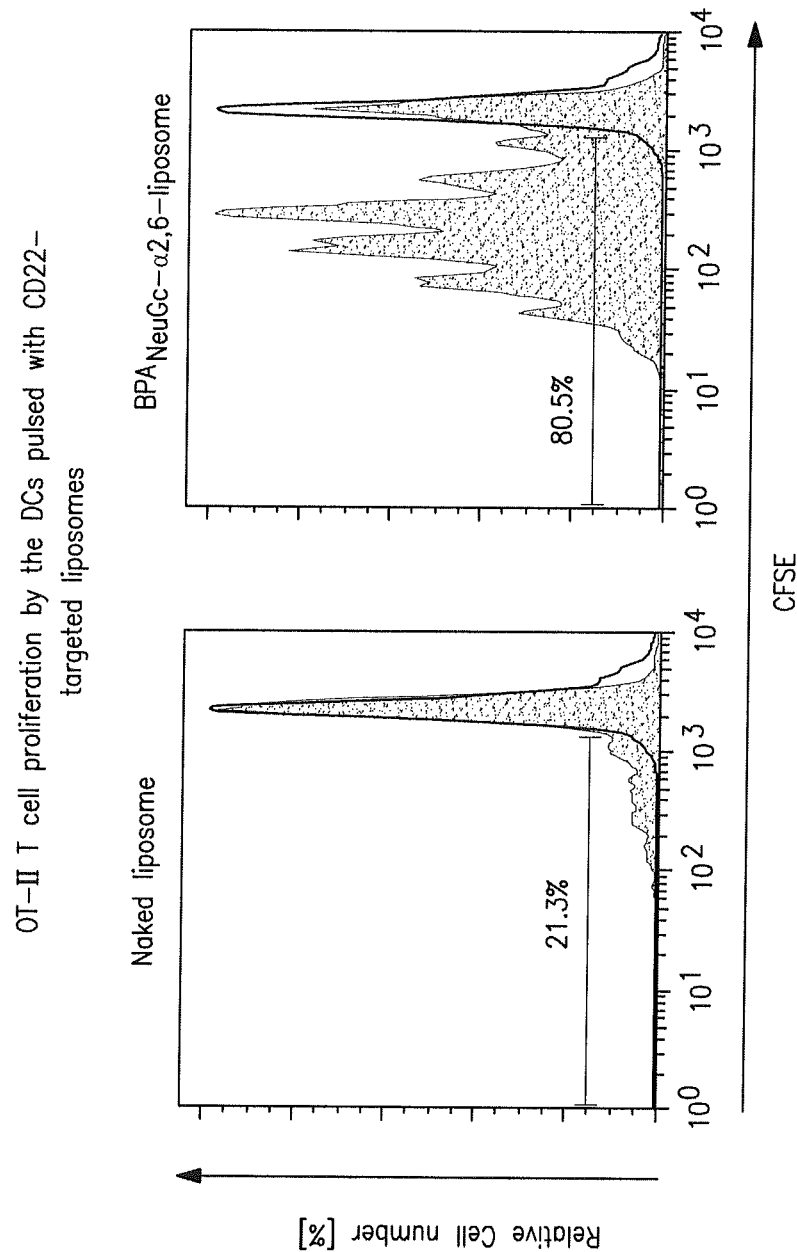

US 9,326,939 B2

LIPOSOME TARGETING COMPOUNDS AND RELATED USES

CROSS-REFERENCE TO RELATED APPLICATIONS

The subject patent application is a 35 USC 371 national phase application of international application no. PCT/US2011/001339, which claims the benefit of priority to U.S. Provisional Patent Application No. 61/400,610 (filed Jul. 31, 2010). The full disclosure of the priority applications are incorporated herein by reference in their entirety and for all purposes.

STATEMENT OF GOVERNMENT SUPPORT

This invention was made with government support under Contract Nos. GM060938 and AI050143 awarded by the National Institutes of Health. The government has certain rights in this invention.

BACKGROUND OF THE INVENTION

Various approaches of targeted therapies have been developed over the years. One approach has been to couple a drug or effector to a targeting agent such as an antibody. The antibody is used to change the distribution of drug or effector such that more of it can localize where it is most needed in vivo. Antibody-mediated cell depletion therapy has proven to provide significant clinical benefit in treatment of lymphomas and leukemia, driving the development of improved therapies with novel mechanisms of cell killing.

As an alternative to antibodies, nanoparticles that are targeted to single cell types have gained attention for their potential to provide selective delivery of therapeutic agents with reduced side effects. Liposomal nanoparticles are pharmaceutically proven delivery vehicles that can encapsulate a therapeutic agent and also display ligands that target cell-surface receptors. The challenge has been to identify a ligand that provides sufficient selectivity for the targeted cell. Certain high-affinity small-molecule ligands (e.g., folate) are efficient at targeting cognate receptors expressed at higher levels on the target cell, but lower expression levels on other cell types reduce selectivity. Immuno-liposomes use antibodies as targeting agents, but have not to date provided a therapeutic index commensurate with their promise.

There is a need in the art for better means for targeted delivery of therapeutic agents to single cell types in order to increase efficacy/potency and reduce side effect. The instant invention addresses this and other needs.

SUMMARY OF THE INVENTION

In one aspect, the invention provides liposome targeting compounds which comprise a liposome nanoparticle displaying a binding moiety for a sialic acid binding Ig-like lectin (Siglec) on a target cell. In some embodiments, the biding moiety on the liposomes is a glycan ligand for the Siglec receptor on the target cell. Examples of such glycan ligands include 9-N-biphenylcarboxyl-NeuAcα2-3Galβ1-4GlcNAc (3'-$^{BPC}$NeuAc), 9-N-biphenylacetyl-NeuGcα2-6Galβ1-4GlcNAc ($^{BPA}$NeuGc), or 9-N-biphenylcarboxyl-NeuAcα2-6Galβ1-4GlcNAc (6'-$^{BPC}$NeuAc). These liposome targeting compounds are particularly useful for targeting antigen presenting cells, e.g., B cells, macrophage, or dendritic cells (DCs). These cells express on their surface Siglec-1 (macrophage) or Siglec-2 (B cells and DCs).

The liposome targeting compounds of the invention typically encapsulate a biological agent, e.g., a drug, an antigen or an immune modifying agent that is to be delivered to the target cell. Some of the liposome targeting compounds encapsulate an antigen such as a protein, a peptide, a lipid-linked antigen, or a polysaccharide. Some other liposome targeting compounds can encapsulate a therapeutic drug (e.g., an anti-tumor agent), an immune modifying agent (e.g., a cytokine) or a polynucleotide (e.g., siRNA).

In a related aspect, the invention provides methods for targeting an antigen to an antigen presenting cell. These methods entail (a) preparing a liposome targeting compound which encapsulates the antigen and also displays a glycan ligand for the Siglec on the antigen presenting cell, and (b) contacting the liposome targeting compound with the antigen presenting cell. These methods can be readily employed to target an antigen to a B cell, a macrophage, or a dendritic cell. In some preferred embodiments, the glycan ligand displayed on the liposome is a ligand for Siglec-1 or Siglec-2. For example, the ligand can be 9-N-biphenylcarboxyl-NeuAcα2-3Galβ1-4GlcNAc (3'-$^{BPC}$NeuAc), 9-N-biphenylacetyl-NeuGcα2-6Galβ1-4GlcNAc ($^{BPA}$NeuGc), or 9-N-biphenylcarboxyl-NeuAcα2-6Galβ1-4GlcNAc (6'-$^{BPC}$NeuAc). These methods can be used both in vitro or in vivo targeting of the antigen to the antigen presenting cell. For example, the antigen can be targeted to an antigen presenting cell inside the body of a subject via, e.g., parenteral administration of the liposome targeting compound.

In another aspect, the invention provides methods for modulating an immune response to an antigen. The methods involve (a) preparing a liposome targeting compound which encapsulates the antigen and displays a glycan ligand for the Siglec on an antigen presenting cell, (b) contacting the liposome targeting compound with the antigen presenting cell, and (c) contacting the antigen presenting cell with a lymphocyte or a monocyte. The antigen presenting cell to be targeted in these methods can be a B cell, a macrophage, or a dendritic cell. For example, targeting a protein antigen to an APC (e.g., macrophage or dendritic cells), and then contacting the APC with precursor T cells can lead to activation of $CD4^+$ and $CD8^+$ T cells. Similarly, targeting a lipid activator of NKT cells to macrophage and then contacting the macrophage with NKT cells can induce production of IL-4 and IFN-γ cytokines and activation of NKT cells.

A further understanding of the nature and advantages of the present invention may be realized by reference to the remaining portions of the specification and claims.

DESCRIPTION OF THE DRAWINGS

FIGS. 2A-2G show that $^{BPC}$NeuAc liposomes are bound and internalized by CD22-expressing cells. (A) FACS analysis for binding of fluorescently (NBD) labeled liposomes to wild-type CHO cells or CHO cells expressing recombinant human CD22. Cells were incubated with the naked or $^{BPC}$NeuAc liposomes or left untreated at 37° C. for 1.5 hours before analysis. (B) CHO cells expressing CD22 were compared for their binding to the fluorescent naked or $^{BPC}$NeuAc liposomes. CD22 was detected with anti-human CD22, and the nuclei were visualized by staining with DAPI. (C) Fluorescence microscopy analysis of the colocalization of $^{BPC}$NeuAc liposomes with early endosomes. CHO-CD22 cells were incubated with fluorescent liposomes as described. Early endosomes were visualized by staining with an Alexa Fluor 555-labeled anti-EEA1. (D) Binding of $^{BPC}$NeuAc liposomes to Daudi human B lymphoma cells. Daudi cells were incubated in mouse serum with liposomes containing 0% to 5% $^{BPC}$NeuAc lipids or without liposomes before FACS analysis. (E) $^{BPC}$NeuAc liposomes rapidly bind to Daudi cells. Fluorescent naked or $^{BPC}$NeuAc liposomes were added to an aliquot of Daudi cells in mouse serum and incubated at 37° C. for the indicated time before FACS analysis. Data are presented as mean channel of fluorescence (MCF) plus or minus SD. (n=3). (F) Competitive binding of $^{BPC}$NeuAc liposomes to Daudi cells in the presence of the free $^{BPC}$NeuAc ligands. Fluorescent naked or $^{BPC}$NeuAc liposomes were incubated with Daudi cells with the presence of the monovalent $^{BPC}$NeuAc ligands at indicated concentration. Data were analyzed by FACS and shown as normalized MCF plus or minus SD. (n=3). (G) Cytotoxicity of dox-loaded liposomes toward Daudi B cells. Cells were subjected to free dox, dox-loaded naked liposomes, or $^{BPC}$NeuAc liposomes for 1 hour at 37° C. Cells were washed and incubated at 37° C. for an additional 48 hours before measuring cell viability. Data shown are means of triplicate plus or minus SD. Representative data from 1 of 3 independent experiments are shown. Data were fitted using the Prism nonlinear regression software.

FIGS. 3A-3G show pharmacokinetics and Siglec specificity of 6'-$^{BPC}$NeuAc liposomes. (A)$^{BPC}$NeuAc liposomes selectively bind to Daudi cells in mouse blood. In vitro (top panels): Daudi cells were spiked into an aliquot of mouse whole blood followed by addition of fluorescent naked or $^{BPC}$NeuAc liposomes. Cells were stained with anti-human CD19 to distinguish Daudi cells from other cells in the mouse blood. In vivo (bottom panels): after intravenous injection of Daudi cells, mice were injected with fluorescent naked or $^{BPC}$NeuAc liposomes. After 2 hours, a blood sample was drawn and the binding of liposomes to Daudi cells was analyzed by FACS. The numbers in the quadrants represent percentages of CD19 Daudi cells that bound or did not bind to liposomes. Shown are data from 1 of 3 independent experiments. (B-C) Dox-loaded liposomes were injected intravenously to the tumor-free SCID mice (3 mice per group) without or with pretreatment of clodronate to deplete tissue macrophages. A sample of blood was withdrawn at 0.5, 2, and 25 hours after liposome injections. The plasma concentration of dox was measured, and data are presented as percentage remaining of the initial injected drug plus or minus SD. (D) FACS analysis for binding of naked or $^{BPC}$NeuAc liposomes to Siglec-expressing CHO lines and Daudi, A20, and TSn cell lines that express hCD22, mCD22 and hSn, respectively. Binding is shown as MCF plus or minus SD (n=3). Binding degree of $^{BPC}$NeuAc liposomes to CHO-mSn, CHO-hCD22, Daudi, and TSn cell lines was significant in comparison to the same cell line that was treated with the naked liposomes (*P<0.01). (E) Comparison of $^{BPC}$NeuAc or $^{BPA}$NeuAc liposomes in binding to cell lines expressing hCD22, mCD22, hSn, and mSn. Binding of liposomes is expressed as MCF plus or minus SD (n=3). (F) Top panel shows that the structures of the trisaccharide ligands designed to be specific for human CD22 are based on the parent compound NeuAcα2-6Galβ1-4GlcNAc, varying the biphenyl substituent at C-9 (R1). Bottom panel shows that $^{BPA}$NeuAc liposomes exhibit a long circulation time in vivo. A sample of blood was withdrawn from mice (n=3) that received dox-loaded naked, $^{BPC}$NeuAc, or $^{BPA}$NeuAc liposomes at 0.5, 2, and 25 hours after liposome injections. The plasma concentration of dox was detected using a fluorometer. Data are presented as percentage remaining of the initial dose±SD. (G) Pharmacokinetics analysis for naked and $^{BPC}$NeuAc liposomes in wild-type C57BL/6 and Sn knockout mice. Data are presented as percentage remaining of the initial dose±SD (n=3).

FIGS. 5A-5B show that CD22-targeting liposomes bind to and kill malignant cells from patients with B-cell lymphomas or leukemias. (A) Correlation of binding of $^{BPC}$NeuAc liposomes with CD22 or CD20 expression on the B-cell lymphomas. The diagonal lines represent linear regression that was analyzed using Prism software and the values of goodness of fit ($r^2$) are indicated (n=25). (B) Cytotoxicity of the dox-loaded $^{BPC}$NeuAc liposomes toward malignant B cells. Top panel shows results of the viability of blood lymphocytes evaluated by the standard MTT assay after treatments of dox-loaded naked or $^{BPC}$NeuAc liposomes with dox concentrations at 10 or 40 µM. Cells left untreated (Unt) were defined as the maximal cell viability. Complete cell killing was determined from the Triton X-100 lysed cells (Tri). Bottom panel shows percentages (means of triplicate±SD) of the viable blood lymphocytes after treatment with dox-loaded naked or $^{BPC}$NeuAc liposomes. *P<0.05 compared with control treatments of naked liposomes. Representative data from 1 of 4 samples are shown.

FIG. 16 shows OT-II T cell proliferation induced by the DCs pulsed with CD22-targeting liposomes.

DETAILED DESCRIPTION

I. Overview

Figure 1A:
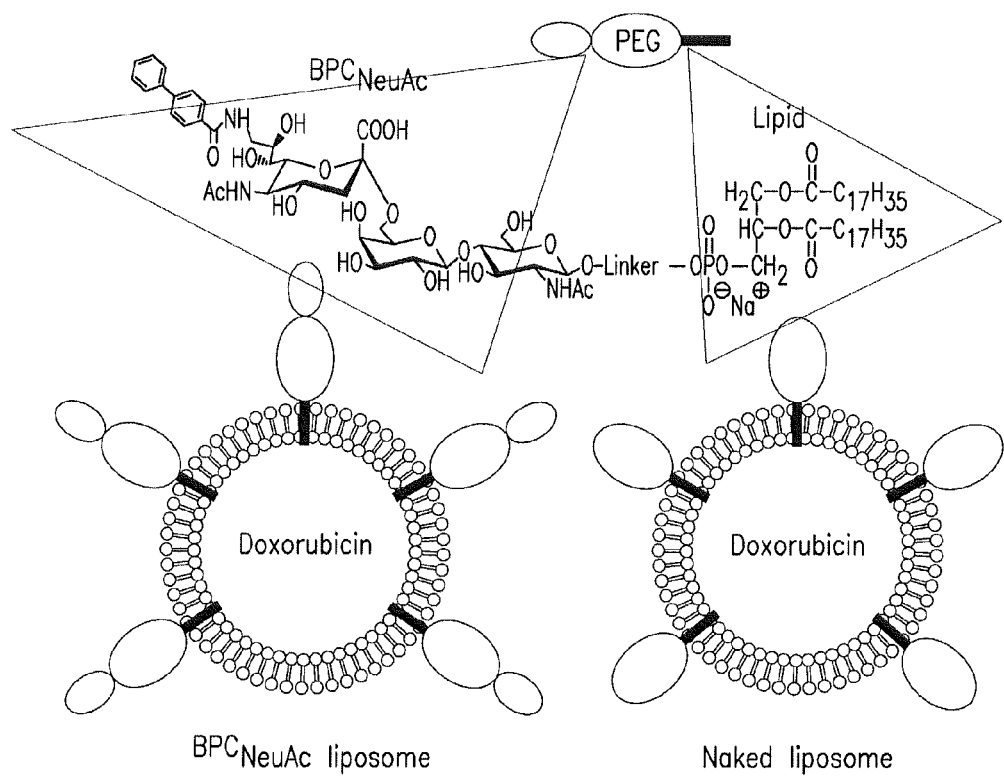
FIGS. 1A-1B show liposomal nanoparticles displaying glycan ligands of CD22 for targeting B-cell lymphoma. (A) Schematic illustration of a chemotherapeutic-loaded liposomal formulation comprising $^{BPC}$NeuAc lipids for active targeting to CD22. (B) Synthesis of $^{BPC}$NeuAc-pegylated lipids.

The present invention is predicated in part on the present inventors' development of liposomal nanoparticles displaying glycan ligands for targeting various cell populations. Specifically, the inventors developed CD22 ligand-decorated liposomal nanoparticles for targeting B lymphoma cells in vivo. There liposomes bear 9-N-biphenylcarboxyl-NeuAcα2-6Galβ1-4GlcNAc ("6-$^{BPC}$NeuAc" or "$^{BPC}$-NeuAc"). It was found that dox-loaded liposomes bearing this ligand of CD22 are actively targeted to and endocytosed by B cells, and significantly extend life in a murine model of human B-cell lymphoma. In addition, the ligand-decorated liposomes recognize and kill malignant B cells in peripheral blood samples from patients with lymphoma in proportion to the amount of CD22 expressed.

The inventors also developed liposomal nanoparticles with encapsulated or incorporated antigens for targeting antigen presenting cells and accordingly modulating immune cells and immune responses. These liposome targeting compounds typically bear glycan ligands for Siglecs that are expressed on macrophages, dendritic cells and B cells. These cells collectively carry MHC Class I and Class II receptors that present peptide antigen to $CD8^+$ and $CD4^+$. T cells, respectively. Polypeptides taken up by antigen presenting cells can be broken down to peptide antigens and loaded onto MHC receptors for subsequent presentation to T cells. Alternatively, polynucleotides (DNA or RNA) encoding antigens can be translated and processed into antigens for presentation by MHC receptors. Antigen presenting cells also carry CD1 receptors that can present lipid and glycolipids antigens to NK T cells. It was shown that incorporation of polypeptide and glycolipid antigens into these liposomal formulations allows active targeting of antigen presenting cells, resulting in an immune response with robust activation of T cells or NKT cells depending on the antigen delivered. As detailed in the Examples below, it was found that targeted delivery of an antigen to macrophage via liposomes (3'-$^{BPC}$NeuAc liposomes) bearing a ligand (9-N-biphenylcarboxyl-NeuAcα2-3Galβ1-4GlcNAc) for sialoadhesin (Siglec-1 or Sn) resulted in presentation of the antigen and activation of CD4+ and CD8+ T cells. Specifically, it was observed that the Sn-targeting liposomes are highly specific for Sn and not other Siglecs, and that the Sn-targeting liposomes bind to and are internalized by macrophages and cell lines expressing Sn. It was additionally observed that the Sn-targeting liposomes can deliver a protein antigen (ovalbumin) to macrophages in vitro, resulting in activating CD4+ T cells (OVA II cells) and CD8+ T cells (OVA I cells).

The Sn-targeting liposomes are also rapidly cleared from circulation in wild type mice, but exhibit long circulatory half life in sialoadhesin deficient (knockout) mice. In vivo, the Sn-targeting liposomes are also able to deliver a protein antigen (ovalbumin) to macrophages, resulting in in vivo activation of CD4+ T cells (OVA II cells). Furthermore, it was found that targeted delivery of a lipid-linked antigen (an activator of NKT cells) to macrophage resulted in antigen presentation, activation of NKT cells, and induction of IL-4 and IFN-γ production in vivo.

Other than targeting Siglec-1 on macrophage, the inventors also developed liposome targeting compounds for delivering antigens to other antigen presenting cells. These liposomes ($^{BPA}$NeuGc-α2,6-liposomes) bear a glycan ligand (9-N-biphenylacetyl-NeuGcα2-6Galβ1-4GlcNAc) that specifically target CD22 (Siglec-2), which is found to be expressed on B cells and dendritic cells. These liposomes bind specifically to B cells and dendritic cells of wild type but not CD22 deficient (knockout) mice. It was also found that delivery of a protein antigen via the CD22-targeting liposomes to dendritic cells resulted in robust antigen presentation and activation of CD4+ T-cells (OVA II cells).

In accordance with these exemplified studies, the present invention provides novel liposome targeting compounds for targeting antigens or therapeutic agents. The invention also provides methods for selectively killing or inhibiting a specific cell population and methods for modulating (e.g., inducing or suppressing) an immune response in cells (e.g., T cells and NK T cells) to a specific antigen. The following sections provide more detailed guidance for practicing the invention.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press ($1^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons ($3^{rd}$ ed., 2002); *Dictionary of Chemistry*, Hunt (Ed.), Routledge ($1^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (Oxford Paperback Reference), Martin and Hine (Eds.), Oxford University Press ($4^{th}$ ed., 2000). Further clarifications of some of these terms as they apply specifically to this invention are provided herein.

The term "agent" includes any substance, molecule, element, compound, entity, or a combination thereof. It includes, but is not limited to, e.g., protein, polypeptide, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "analog" or "derivative" is used herein to refer to a molecule that structurally resembles a reference molecule but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs to identify variants of known compounds having improved traits (such as higher binding affinity for a target molecule) is an approach that is well known in pharmaceutical chemistry.

The term antigen broadly refers to a molecule that can be recognized by the immune system. It encompasses proteins, polypeptides, polysaccharides, as well as polypeptide- or polysaccharide-linked lipids ("lipid-linked antigens") or nucleic acids ("nucleic acid-linked antigens").

Antigen presenting cells (APCs) are cells that can present antigen in a form that T cells can recognize. The immune system contains three types of APCs: macrophages, dendritic cells and B cells. These cells, also known as professional APCs, express MHC class II and are able to activate a helper T-cell that has never encountered its antigen before. The APCs can also present antigens to cytotoxic T cells via the MHC class I pathway. They can engulf the antigen quickly during a process called phagocytosis. Once the T-cell recognizes and binds to the MHC molecule complex, the APC sends out an additional co-stimulatory signal to activate the T-cell.

Dendritic cells (DCs) are immune cells that form part of the mammalian immune system. Their main function is to process antigen material and present it on the surface to other cells of the immune system, thus functioning as antigen-presenting cells. They act as messengers between the innate and adaptive immunity. Dendritic cells are present in small quantities in tissues that are in contact with the external environment, mainly the skin (where there is a specialized dendritic cell type called Langerhans cells) and the inner lining of the nose, lungs, stomach and intestines. They can also be found in an immature state in the blood. Once activated, they migrate to the lymphoid node where they interact with T cells and B cells to initiate and shape the adaptive immune response. At certain development stages they grow branched projections, the dendrites, that give the cell its name. However, these do not have any special relation with neurons, which also possess similar appendages. Immature dendritic cells are also called veiled cells, in which case they possess large cytoplasmic 'veils' rather than dendrites.

Macrophages are white blood cells within tissues, produced by the differentiation of monocytes. Monocytes and macrophages are phagocytes, acting in both non-specific defense (innate immunity) as well as to help initiate specific defense mechanisms (adaptive immunity) of vertebrate animals. Their role is to phagocytose (engulf and then digest) cellular debris and pathogens either as stationary or as mobile cells, and to stimulate lymphocytes and other immune cells to respond to the pathogen. They can be identified by specific expression of a number of proteins including CD14, CD11b, F4/80 (mice)/EMR1 (human), Lysozyme M, MAC-1/MAC-3 and CD68 by flow cytometry or immunohistochemical staining.

B cells are the least efficient antigen presenting cells. Unlike the other two types of APCs, they possess specific antigen receptors, surface immunoglobulins. B cells ingest soluble proteins by pinocytosis. They also possess specific uptake receptors in surface immunoglobulins. B cells present antigen via MHC-II. But these cells do not express co-stimulatory molecules. In order to do so, they need to be activated by T helper cells.

As used herein, liposomes or liposome nanoparticles refer to ultra fine liposome vesicles sized between about 10 and about 200 nanometers. Like other liposomes, they are typically made of lipid bilayer. Liposome nanoparticles are nanoparticles of semi-solid nature. They can be filled with drugs, and used to deliver drugs for cancer and other diseases. Various types of liposome nanoparticles are currently used clinically as delivery systems for anticancer drugs and vaccines.

Siglecs, short for sialic acid binding Ig-like lectins, are cell surface receptors and members of the immunoglobulin superfamily (IgSF) that recognize sugars. Their ability to recognize carbohydrates using an immunoglobulin domain places them in the group of I-type (Ig-type) lectins. They are transmembrane proteins that contain an N-terminal V-like immunoglobulin (IgV) domain that binds sialic acid and a variable number of C2-type Ig (IgC2) domains. The first described Siglec is sialoadhesin (Siglec-1/CD169) that is a lectin-like adhesion molecule on macrophages. Other Siglecs were later added to this family, including Siglec-G/10 (i.e., human Siglec-10 and mouse Siglec-G), CD22 (Siglec-2), which is restricted to B cells and has an important role in regulating their adhesion and activation, CD33 (Siglec-3) and myelin-associated glycoprotein (MAG/Siglec-4). Several additional Siglecs (Siglecs 5-12) have been identified in humans that are highly similar in structure to CD33 so are collectively referred to as 'CD33-related Siglecs'. CD33-related Siglecs all have two conserved immunoreceptor tyrosine-based inhibitory motif (ITIM)-like motifs in their cytoplasmic tails suggesting their involvement in cellular activation.

Unless otherwise noted, a "liposome targeting compound" (or a "liposome targeting composition" or a "liposome targeting nanoparticle") as used herein refers to a complex that contains a lipid component that forms a bilayer(s) around an internal aqueous solution. The compound can display on or incorporate into the lipid moiety a binding moiety (e.g., a glycan ligand) that is specific for a target molecule (e.g., a Siglec) on a target cell. Typically, the binding moiety is integrated into the lipid component of the liposome complex. The liposome compound can additionally encapsulate or contain a biological agent (e.g., a therapeutic agent or an antigen) that is to be delivered to a target cell. The biological agent "encapsulated" or "incorporated" by the liposome compound typically partitions into the lipid component and/or is wholly or partially soluble in the interior aqueous solution of the liposome complex.

"Target cell" refers to a eukaryotic cell, e.g., an animal, mammalian, or particularly human cell, that expresses a cognate target molecule (e.g., a receptor) on its surface. A target cell may be isolated or may be present in the body of an animal or human, to whom the liposome complex is administered. In some preferred embodiments, the target cell is an antigen presenting cell including a macrophage, a dendritic cell or a B cell.

Administration "in conjunction with" one or more other therapeutic agents includes simultaneous (concurrent) and consecutive administration in any order.

The term "contacting" has its normal meaning and refers to combining two or more agents (e.g., polypeptides or small molecule compounds) or combining agents and cells. Contacting can occur in vitro, e.g., combining an agent with a cell or combining two cells in a test tube or other container. Contacting can also occur in vivo, e.g., by targeted delivery of an agent to a cell inside the body of a subject.

The term "immune cell" refers to leukocytes of the immune system which are involved in defending the body against both infectious disease and foreign materials. More specifically, the term as used in the invention refers to mononuclear leukocytes including lymphocytes, monocytes, and macrophages. In some embodiments of the invention, modulating of immune cells means regulation of the cellular functions of B lymphocytes and T lymphocytes (including CD4+ T helper cell, CD8+ cytotoxic T cell, and NKT cell).

The term "modulate" with respect to an immune cell or an immune response refers to a change in the activities or cellular processes mediated by the immune cell or the immune system (e.g., antigen processing and presentation by macrophage, T cell activation and proliferation, and cytokine production). Modulation can be up-regulation (i.e., activation or stimulation) or down-regulation (i.e. inhibition or suppression). The change in the modulated activity or immune response can be direct (e.g., through binding of an agent to the cell) or indirect (e.g., through interaction of the agent with another molecule or another cell which otherwise modulates the cell).

The term "subject" refers to any animal classified as a mammal, e.g., human and non-human mammals. Examples of non-human animals include dogs, cats, cattle, horses, sheep, pigs, goats, rabbits, and etc. Unless otherwise noted, the terms "patient" or "subject" are used herein interchangeably. Preferably, the subject is human.

The term "treating" or "alleviating" includes the administration of compounds or agents to a subject to prevent or delay the onset of the symptoms, complications, or biochemical indicia of a disease (e.g., an tumor, an microbial infection, or an inflammatory), alleviating the symptoms or arresting or inhibiting further development of the disease, condition, or disorder. Subjects in need of treatment include those already suffering from the disease or disorder as well as those being at risk of developing the disorder. Treatment may be prophylactic (to prevent or delay the onset of the disease, or to prevent the manifestation of clinical or subclinical symptoms thereof) or therapeutic suppression or alleviation of symptoms after the manifestation of the disease.

III. Liposome Targeting Compounds with Encapsulated Biological Agents

The present invention provides liposome targeting compounds (or liposome targeting compositions or complexes) which display a binding moiety that specifically recognizes a target cell or tissue. The liposome target compounds can additionally incorporate or encapsulate therein a biological agent or payload that is to be delivered to the target cell. The payload carried or encapsulated in the liposome can be any biological agents, such as antigens, drugs, polynucleotides such as cDNAs or inhibitory polynucleotides like siRNAs that are desired to be delivered to a specific target cell. For example, the target can be a diseased cell or tissue (e.g., tumor) to which a therapeutic agent is to be delivered. The target can also be an effector or precursor cell (e.g., an antigen presenting cell) to which a regulating or activating agent (e.g., an antigen) is to be delivered. For example, some embodiments of the invention are directed to liposome targeting compositions for targeting antigen presenting cells, e.g., macrophages, dendritic cells and B cells. To specifically target a desired target cell, the liposome targeting compound incorporates on the liposome a binding moiety that specifically binds to a receptor molecule on the target cell. In some preferred embodiments, the target cell is one that expresses on its surface a Siglec. In these embodiments, the liposome targeting compound incorporates or displays a glycan ligand that specifically recognizes the Siglec.

The liposome component of the target compounds of the invention is typically a vesicular structure of a water soluble particle obtained by aggregating amphipathic molecules including a hydrophilic region and a hydrophobic region. While the liposome component is a closed micelle formed by any amphipathic molecules, it preferably includes lipids. For example, the liposomes of the invention exemplified herein contain phospholipids such as distearoyl phosphatidylcholine (DSPC) and polyethyleneglycol-distearoyl phosphoethanolamine (PEG-DSPE). Other phospholipids can also be used in preparing the liposomes of the invention, including dipalmitoylphosphatidylcholine (DPPC), dioleylphosphatidylcholine (DOPC) and dioleylphosphatidyl ethanolamine (DOPE), sphingoglycolipid and glyceroglycolipid. These phospholipids are used for making the liposome, alone or in combination of two or more or in combination with a lipid derivative where a non-polar substance such as cholesterol or a water soluble polymer such as polyethylene glycol has been bound to the lipid.

For delivery of the payload to a specific target, the liposome targeting complex displays or incorporates on its surface a binding moiety or ligand that specifically recognizes a receptor or surface molecule on the target cell. The binding moiety is a molecule that recognizes, binds or adheres to a target molecule located in a cell, tissue (e.g. extracellular matrix), fluid, organism, or subset thereof. The binding moiety and its target molecule represent a binding pair of molecules, which interact with each other through any of a variety of molecular forces including, for example, ionic, covalent, hydrophobic, van der Waals, and hydrogen bonding, so that the pair have the property of binding specifically to each other. Specific binding means that the binding pair exhibit binding with each other under conditions where they do not bind to another molecule. Examples of binding pairs are biotin-avidin, hormone-receptor, receptor-ligand, enzyme-substrate, IgG-protein A, antigen-antibody, and the like. The targeting agent and its cognate target molecule exhibit a significant association for each other. This association may be evaluated by determining an equilibrium association constant (or binding constant) according to methods well known in the art. Affinity is calculated as $K_d = k_{off}/k_{on}$ ($k_{off}$ is the dissociation rate constant, $k_{on}$ is the association rate constant and $K_d$ is the equilibrium constant.

By employing different binding moieties, the payload encapsulated or carried in the liposome can be specifically delivered to various target sites (target cell or tissue). For example, the target site can be the liver, spleen, lymph node, bone marrow, lung, eye, skin and nose. The binding moieties that can be incorporated on the surface of the liposome can be any compound that specifically recognizes the target cell. In some preferred embodiments, the binding moiety is a glycan ligand that specifically recognizes a Siglec on the surface of an antigen presenting cell. Examples of suitable glycan ligands for the present invention are described in the Examples below, e.g., 9-N-biphenylcarboxyl-NeuAcα2-3Galβ1-4GlcNAc (3'-$^{BPC}$NeuAc), 9-N-biphenylacetyl-NeuGcα2-6Galβ1-4GlcNAc ($^{BPA}$NeuGc), or 9-N-biphenylcarboxyl-NeuAcα2-6Galβ1-4GlcNAc (6'-$^{BPC}$NeuAc). Derivative or analog compounds of these exemplified glycan ligands can also be used in the invention. Also suitable for practicing the present invention are some other glycan ligands of Siglecs that are known in the art, e.g., as described in WO 2007/056525.

In some other embodiments, the employed binding moieties can be other types of small molecular compounds, high molecular compounds, nucleic acids, peptides, proteins and sugar chains. For example, suitable high molecular compounds include polyethylene glycol (see U.S. Pat. No. 2,948, 246). The nucleic acid compounds include, for example, single strand RNA and single strand DNA which recognize TLR-7 or TLR-9 of the Toll-like receptor in the target cell, and derivatives of these nucleic acids. The protein compounds include, for example, antibodies and receptors which recognize the molecules expressed specifically on the surface of the target cells such as dendritic cells (DC) which are antigen presenting cells or precursor cells thereof. The modification with the sugar chain includes the modification with mannose bound lipid which can be bound to a mannose receptor expressed on the surface of DC (e.g., see Copland et al., *Liposome delivery of antigen to human dendritic cells*, Vaccine, 21:883-890, 2003).

In addition to the binding moiety, the liposome targeting compositions of the invention typically also contain (e.g., encapsulate therein) a biological agent (or payload). The biological agent contained in the liposome can be any compound that is able to modulate the target cell. They include, e.g., small molecule drugs (e.g., pharmaceutical organic compounds of about 5,000 daltons or less), organic molecules, proteins, peptides, peptidomimetics, glycoproteins, proteoglycans, lipids glycolipids, phospholipids, lipopolysaccharides, nucleic acids, proteoglycans, carbohydrates, and the like. Biological agents may be any of the anti-neoplastic agents, anti-microbial agents or hormone agents that are well known in the art or described herein. They also include non-steroidal anti-inflammatories such as indomethacin, salicylic acid acetate, ibuprofen, sulindac, piroxicam, and naproxen, and anesthetics or analgesics. Also included are radioisotopes such as those useful for imaging as well as for therapy.

For therapeutic application, the biological agent is a therapeutic compound that kills or inhibits the growth of the target cell. Various therapeutic agents can be used in the practice of the present invention. Examples include the anti-neoplastic drugs noted above, e.g., cancer drugs doxorubicin, carminomycin, pyrrolinodoxorubicin precursor, Taxol (Paclitaxel), etoposide, captothecin, and enediyne. Other drugs (e.g., antimicrobial drugs) described herein or that are well known in the art (see, e.g., Springhouse, *Physician's Drug Handbook*, Lippincott Williams & Wilkins ($12^{th}$ edition, 2007)) can also be employed in the practice the present invention.

In some other embodiments, the liposome targeting compounds are intended for delivering a modulating agent to a target cell to induce or regulate an activity or cellular process (e.g., antigen presentation) mediated by the target cell. For these regulatory applications, the biological agent can be a compound that activates or stimulates the target cell. Specific examples include liposome complexes that deliver antigens to macrophage in order to activate T cells or natural killer cells and induce cytokine production (e.g., IL-4 and IFN-γ production), as described in the Examples below. For example, targeted delivery of α-gal-ceramide, a poten antigen for the invariant NKT cell receptor, was much more effective in stimulating NKT cells than the antigen alone. Other examples of biological agents to be delivered with the liposome targeting complexes of the invention include agents that suppress undesired activation of the target cell, e.g., inhibition of Th1 cell activation in allergic disorders.

The liposome component of the targeting complex of the invention can be prepared in accordance with methods well known in the art. For example, incorporation of a binding moiety on the surface of a liposome and encapsulation of a biological agent therein can be achieved by any of the routinely practiced procedures. Detailed procedures for producing a liposome nanoparticle bearing a binding moiety are also exemplified in the Examples herein. These include liposomes with an incorporated glycan ligand such as 3'-$^{BPC}$NeuAc, $^{BPA}$NeuGc, or 6'-$^{BPC}$NeuAc. Similarly, an antigen or a therapeutic drug can also be incorporated or encapsulated in the glycan ligand bearing liposomes in accordance with the protocols disclosed in the Examples.

In addition to these specifically disclosed methods for preparing liposomes, various methods routinely used by the skilled artisans can also be employed in the present invention. For example, the methods described in *Liposome Technology*, vol. 1, $2^{nd}$ edition (by Gregory Gregoriadis (CRC Press, Boca Raton, Ann Arbor, London, Tokyo), Chapter 4, pp 67-80, Chapter 10, pp 167-184 and Chapter 17, pp 261-276 (1993)) can be used. More specifically, suitable methods include, but are not limited to, a sonication method, an ethanol injection method, a French press method, an ether injection method, a cholic acid method, a calcium fusion method, a lyophilization method and a reverse phase evaporation method. A size of the liposome of the present invention is not particularly limited, and typically is preferably between 1 to 200 nm and more preferably between 10 to 100 nm in average. The structure of the liposome is not particularly limited, and may be any liposome such as unilamella and multilamella. As a solution encapsulated inside the liposome, it is possible to use buffer and saline and others in addition to water.

IV. Uses of Liposome Targeting Compositions

The invention provides methods of using the liposome compounds disclosed herein in targeted delivery of an incorporated or encapsulated payload to a target cell. In some preferred embodiments, the liposome targeting compositions are employed for targeted delivery of an antigen to an antigen presenting cell. As exemplified herein, the antigen (e.g., a polypeptide antigen or a lipid-linked antigen) can be targeted to a macrophage, a dendritic cell, or a B cell with a liposome bearing a glycan ligand of Siglec-1 or Siglec-2. Liposome compositions encapsulating the antigen for targeting antigen presenting cells can be used to deliver the antigen to a target antigen presenting cell either in vitro or in vivo. The invention also provides methods for using the liposome targeting compounds in the treatment of various diseases and disorders. These include, e.g., treating cancers by delivering an anti-tumor agent to tumor cells. The invention further provides uses of the liposome targeting compounds in the manufacture of a medicament for treating various medical conditions or modulating immune response as described herein. In any of these applications, the liposome compositions encapsulating a therapeutic agent can be used alone or administered in conjunction with other known drugs in the treatment of a specific disease or condition. The invention further provides for a pharmaceutical combination (e.g., a kit) for carrying out these therapeutic applications. Such pharmaceutical combination can contain a liposome targeting compound disclosed herein, in free form or in a composition, an optional co-agent or carrier, as well as instructions for administration of the agents.

Some embodiments of the invention are directed to therapeutic applications of the liposome targeting compounds. In some of these embodiments, the liposome targeting compounds described herein are employed to deliver various drugs (e.g., anti-neoplastic drugs, anti-microbial drugs or hormone agents described herein) in vitro or in vivo. These methods are useful in targeted chemotherapy of cancers or other diseases. Accordingly, the invention also provides methods of treating subject in need of treatment (e.g., human patients) by administering to the subject a liposome targeting compound of the invention. Typically, the liposome targeting compound and the drug to be administered to the subject should correspond to the specific disease or condition that needs to be treated or ameliorated. For example, for a subject suffering from a cancer (e.g., breast tumor or prostate cancer, etc.), the drug to be administered should be an anti-neoplastic drug (e.g., doxorubicin). In addition, as described above, the specific liposome targeting compound used in the treatment should contain a targeting agent or binding moiety that can direct the liposome compound to the intended disease site (e.g., tumor endothelial cell).

A great number of diseases and conditions are amenable to treatment with methods and compositions of the present invention (e.g., tumors or angiogenesis-associated disorders). Depending on the specific binding moiety and/or biological agent (e.g., a drug) employed in the therapeutic applications, different diseases can be treated or ameliorated with the therapeutic compounds of the invention. For example, as exemplified herein, liposome targeting compounds encapsulating an anti-tumor drug and bearing a glycan ligand for CD22 on B cell can be used to treat B cell lymphoma.

Similarly, liposome compounds which employ a binding moiety for integrin (e.g., integrin $\alpha_v\beta_3$ antagonists) can be used in the treatment of several human diseases, including diseases involving neovascularization, such as rheumatoid arthritis, cancer, and ocular diseases. Other examples of tumors that can be treated include cardiac cancer, lung cancer, various gastrointestinal cancers, genitourinary tract cancer, bone cancer, cancers of the nervous system, gynecological cancers, skin cancer and cancers of the adrenal glands (e.g., neuroblastoma). Using anti-microbial drugs and appropriate binding moieties, the liposome targeting compounds of the invention can also be used in the treatment of various viral and bacterial infections. For any given disease, one can prepare a suitable liposome targeting compound which contains an appropriate binding moiety and an appropriate therapeutic agent in accordance with the present disclosure and knowledge well known in the art, e.g., Springhouse, *Physician's Drug Handbook*, Lippincott Williams & Wilkins (12$^{th}$ edition, 2007).

The liposome targeting compounds described herein can be administered alone or as a component of pharmaceutical compositions. Pharmaceutical compositions of the invention comprise an effective amount of a therapeutic compound of the invention (e.g., a therapeutic agent incorporated or encapsulated in the liposome targeting compound) formulated with at least one pharmaceutically acceptable carrier.

Pharmaceutical compositions of the invention can be prepared and administered to a subject by any methods well known in the art of pharmacy. See, e.g., *Goodman & Gilman's The Pharmacological Bases of Therapeutics*, Hardman et al., eds., McGraw-Hill Professional (10$^{th}$ ed., 2001); *Remington: The Science and Practice of Pharmacy*, Gennaro, ed., Lippincott Williams & Wilkins (20$^{th}$ ed., 2003); and Pharmaceutical *Dosage Forms and Drug Delivery Systems*, Ansel et al. (eds.), Lippincott Williams & Wilkins (7$^{th}$ ed., 1999). In addition, the therapeutic compounds of the invention may also be formulated to include other medically useful drugs or biological agents.

The liposome targeting compositions of the invention can be employed in a variety of therapeutic or regulatory applications towards a target cell. The liposome targeting compounds of the invention can be used to deliver the incorporated or encapsulated payload to the target cell either in vitro or in vivo. For in vitro applications, the liposome complex is contacted directly with the target cell. For example, as exemplified herein, a liposome targeting compound bearing a glycan ligand for macrophage can be mixed with macrophage to deliver an antigen to macrophage for processing and presentation.

In some preferred embodiments, the liposome compositions are used for in vivo applications. In these applications, the liposome complexes set forth herein can be administered to a patient in need of treatment according to protocols already well established in the art. The liposome targeting complex can be administered alone or in combination with a carrier in an appropriate pharmaceutical composition. Typically, a therapeutically effective amount of the liposome complexes is combined with a pharmaceutically acceptable carrier. The pharmaceutically acceptable carrier is any carrier known or established in the art. Exemplary pharmaceutically acceptable carriers include sterile pyrogen-free water and sterile pyrogen-free saline solution. Other forms of pharmaceutically acceptable carriers that can be utilized for the present invention include binders, disintegrants, surfactants, absorption accelerators, moisture retention agents, absorbers, lubricants, fillers, extenders, moisture imparting agents, preservatives, stabilizers, emulsifiers, solubilizing agents, salts which control osmotic pressure, diluting agents such as buffers and excipients usually used depending on the use form of the formulation. These are optionally selected and used depending on the unit dosage of the resulting formulation.

A therapeutically effective amount of the incorporated or encapsulated payload or biological agent varies depending upon the disorder, each specific patient and other well known factors such as age, weight, etc., and thus must be determined empirically in each case. This empirical determination can be made by routine experimentation. Typically, though, the liposome components may be used at a ratio of about 200:1 w/w, e.g., 100-300:1 w/w, compared to the therapeutic payload. A typical therapeutic dose of the liposome composition is about 5-100 mg per dose, e.g., 10 mg per dose.

For in vivo applications, the liposome composition can be administered to the patient by any customary administration route, e.g., orally, parenterally or by inhalation. As shown in the Example below, a macrophage-targeting liposome can be administered to a subject by intravenous injection to deliver an NKT-activating antigen. In some other embodiments, the liposome complex can be administered to a patient intravascularly. A liposome useful for intravascular administration can be a small unilamellar liposome, or may be a liposome comprising PEG-2000. When the composition is parenterally administered, the form of the drug includes injectable agents (liquid agents, suspensions) used for intravenous injection, subcutaneous injection, intraperitoneal injection, intramuscular injection and intraperitoneal injection, liquid agents, suspensions, emulsions and dripping agents.

In some other embodiments, the liposome composition is administered orally to a subject. In these embodiments, a form of the drug includes solid formulations such as tablets, coated tablets, powdered agents, granules, capsules and pills, liquid formulations such as liquid agents (e.g., eye drops, nose drops), suspension, emulsion and syrup, inhales such as aerosol agents, atomizers and nebulizers, and liposome inclusion agents. In still some other embodiments, the liposome composition is administered by inhalation to the respiratory tract of a patient to target the trachea and/or the lung of a patient. In these embodiments, a commercially available nebulizer may be used to deliver a therapeutic dose of the liposome complex in the form of an aerosol.

EXAMPLES

The following examples are offered to illustrate, but not to limit the present invention.

Example 1

Materials and Methods

Preparation of liposomes: The protocols are described for preparing $^{BPC}$NeuAc liposomes. Liposomes bearing other glycan ligands can be similarly prepared. Distearoyl phosphatidylcholine (DSPC), cholesterol (chol), nitrobenzoxadiazol-phosphoethanolamine (NBD-PE), and polyethyleneglycol-distearoyl phosphoethanolamine (PEG-DSPE) were purchased from Avanti Polar Lipids and NOF Corporation. $^{BPC}$NeuAc-PEG-DSPE was prepared by coupling 9-N-biphenylcarboxyl-NeuAcα2-6Galβ1-4GlcNAc (6'-$^{BPC}$-NeuAc) sialosides with an ethylamine linker to N-hydroxysuccinimide (NHS)-activated pegylated lipids (NOF Corporation). Nontargeted naked liposomes were composed of DSPC:Chol:PEG-DSPE in a 60:35:5 molar ratio. CD22-targeting $^{BPC}$NeuAc liposomes substituted $^{BPC}$NeuAc-PEG-DSPE for PEG-DSPE on a mol-for-mol basis. For preparation of liposomes, lipids dissolved in chloroform and dimethyl sulfoxide were mixed and lyophilized for 16 hours.

The lipid flakes were hydrated in the cell culture-grade water to achieve a final liposome concentration of 10 mM (total phospholipids) before extrusion through polycarbonate membrane filters (Millipore) with controlled pore sizes of 0.4, 0.2, and 0.1 µm. To prepare fluorescently labeled liposomes, 1 mol % of NBD-PE was added into the lipid mixture. Remote loading of dox (Sigma) was obtained using gradients of ammonium sulfate.

Liposomes were hydrated in 250 mM ammonium sulfate followed by extrusion and dialysis against 290 mM glucose at 4° C. for at least 4 changes of buffer. Dox was added to the liposome suspension in a ratio of dox/phospholipids equaling 1:7.5 (mass/mass) and incubated at 65° C. for 40 minutes. The unbound drug was separated from liposomes by passing the suspensions through a Sepharose CL-4B (GE Healthcare) column equilibrated in 5% glucose (approximately 20-mL column for 2-mL sample). Concentration of encapsulated dox was determined using a fluorescence plate reader at excitation (Ex) of 485 nm and emission (Em) of 590 nm after complete lysis of liposomes by 0.5% Triton X-100. The loading efficiency of doxorubicin was greater than 90%. Liposomes prepared using this method had a mean particle size of 100 nm plus or minus 10 nm in diameter and were confirmed by a Malvern instrument.

Cell lines and binding assay: Daudi Burkitt lymphoma cells were maintained in RPMI-1640 (Invitrogen) containing 10% fetal bovine serum (FBS). Wild-type Chinese hamster ovary (CHO) cells or CHO cells expressing human CD22 were cultured in Dulbecco modified Eagle medium (DMEM)/F12 supplemented with 10% FBS and 100 µg/mL phleomycin (Invitrogen) or 500 µg/mL Hygromycin-B (Roche), respectively. CHO cell lines expressing Siglec-F and Siglec-E were prepared essentially as described earlier. CHO lines expressing other human or murine Siglecs were generously provided by P.R.C. (University of Dundee, Scotland) and Dr Yasuhiro Hashimoto (Riken, Japan). CHO Siglec lines were maintained in F10 medium (Invitrogen) supplemented with 10% FBS. TSn cells that overexpress human sialoadhesin (Sn) were a gift from Dr Hans Rempel and Dr Lynn Pulliam (University of California, San Francisco). TSn was cultured in RPMI-1640 containing 10% FBS and 1 µg/mL gentamicin (Invitrogen). A20, a murine B-cell line, was maintained in RPMI-1640 with 10% FBS. Unless otherwise stated, the liposome-binding assay was conducted by incubating cells in the mouse or human serum (MP Biomedicals) at $10^6$ cells/100 µL with the presence of fluorescently labeled liposomes at 200 µM (total phospholipids). After incubation at 37° C. for 1.5 hours, cells were washed followed by fluorescence-activated cell sorter (FACS) analysis.

Fluorescence microscopy: CHO cells expressing CD22 were plated to a coverslip to achieve a 90% confluence followed by incubating with fluorescent liposomes at 37° C. for 1 hour. Cells were fixed with 4% paraformaldehyde and stained with PE.Cy5-conjugated anti-human CD22 (BD Pharmingen). For detecting endosomes, fixed cells were permeabilized with 0.05% saponin and stained with anti-EEA1 (BD Pharmingen) followed by AlexaFluor 555-conjugated anti-mouse IgG (Invitrogen). Finally, the specimens were mounted on a slide using mounting solution (Invitrogen) containing DAPI that stains nuclei. Images were taken and processed using a Zeiss fluorescence microscope with a 40×/0.6 oil objective lens (numeric aperature: 0.35; WD: 70 mm), an Axiocam MRm camera (Carl Zeiss), and Axiovision 4 acquisition software.

In vitro cytotoxicity assay: Daudi B lymphoma cells were incubated with dox in free form or entrapped in the naked or $^{BPC}$NeuAc liposomes at 37° C. for 1 hour. Dox concentrations ranging from 1 nM to 1 mM were examined. Cells were washed and seeded on a 96-well plate at $10^5$ cells/100 µL growth media, which allowed for an additional 48 hours of incubation followed by determining cell viability using Cell-Titer 96 (Promega) to measure the activity of enzymes that reduce a tetrazole (MTT) to formazan. The maximum cell viability was defined as medium-treated (untreated) cells. The complete killing was determined as Triton X-100 (0.5%) lysed cells. Data were analyzed using Prism nonlinear regression software (GraphPad Software) for the curve-fitting and determination of $IC_{50}$ values. In the case of the clinical samples, we followed the method described by Kreitman et al. (Clin. Cancer Res. 177:3063, 2000) with modifications. In brief, peripheral blood monocytes were purified using Ficoll-Paque (GE Healthcare) and subjected to liposomal doxorubicin at 10 or 40 µM or medium-treated for 1 hour at 37° C. Cells were thoroughly washed and seeded on a 96-well plate at $10^6$ cells/100 µL in RPMI-1640 supplemented with 10% FBS and 2-mercaptoethanol. Cell viability was determined as described on day 5 of incubation.

Mice and pharmacokinetics studies: The Institutional Animal Care and Use Committee of The Scripps Research Institute (0) approved all experimental procedures involving mice. Nonobese diabetic-severe combined immunodeficiency (NOD-SCID) mice were produced by the TSRI breeding colony. Sialoadhesin (Sn) knockout mice were provided by P.R.C. Naive or Daudi tumor-bearing mice (3 mice per group) were intravenously injected with liposomal dox (3 mg/kg). At 0.5, 2, and 25 hours after liposome injection, a sample of blood (100 µL) was drawn from mice by making a tail nick and collected in a tube containing 10 µL of EDTA to prevent plasma from clogging. Plasma (50 µL) was separated from the blood cells by centrifugation and was mixed with 200 µL of 5% Triton X-100, 250 µL of distilled water, and 1500 µL of acidified isopropanol containing 0.75N HCl. Samples were stored at −20° C. overnight for protein precipitation. After removal of the precipitated protein, an aliquot (100 µL) of the solution containing plasma samples or dox standards were subjected to the analysis for the concentration of the extracted doxorubicin using a fluorescence plate reader at Ex of 485 nm and Em of 590 nm. The data were analyzed using the Prism software. For macrophage depletion, the SCID mice received 200 µL of liposomal clodronate intravenously at 2 days before the injection of the liposomal formulations of dox.

In vivo efficacy studies: Female NOD-SCID mice (6 to 8 weeks old) were injected with 5×$10^6$ Daudi cells at the lateral tail vein intravenously on day 0 (8-10 per group). At days 1 and 3 after tumor injection, animals received intravenous treatments of PBS or 3 mg/kg dox encapsulated in the naked or $^{BPC}$NeuAc liposomes (in 150 µL of 5% glucose). Animals were monitored every other day until the end of the study at day 100 and were killed at the onset of hind-leg paralysis. Survival rate was analyzed using a Kaplan-Meier plot. For detecting residual Daudi tumor cells in the bone marrow, paralyzed or long-term survivor animals were killed, followed by the harvest of bone marrow cells from both femurs. Washed cells were stained with anti-human CD19 or isotype antibodies to identify Daudi tumor cells before FACS analysis.

Clinical subjects: The procedures involving human subjects were reviewed and approved by TSRI Institutional Review Board. We obtained normal blood from TSRI's Normal Blood Donor Service and peripheral blood samples from patients seen by physicians of the Scripps Clinic Medical Group. Eligible patients with untreated or progressive lymphomas and leukemias gave informed consent before participation in this study. Whole blood was freshly collected into EDTA-coated tubes and was analyzed within 24 hours. Fluorescent liposomes were directly added into an aliquot of 100 µL of whole blood and incubated at 37° C. for 1.5 hours, followed by the lysis of red blood cells. Cells were resuspended in 100 µL of Hanks buffered salt solution (HBSS) buffer containing 5% bovine serum albumin (BSA) and incubated with antibodies for detecting surface markers at room temperature for an additional 30 minutes. The following anti-human antibodies purchased from BD Pharmingen were used in the study: anti-CD5 (L17-F12), anti-CD19 (HIB19), anti-CD20 (L27), anti-CD22 (HIB22), anti-CD103 (Ber-ACT8), and anti-(TB28-2) and anti-light chains (1-155-2). Cells were washed twice before FACS analysis. Data were analyzed using FlowJo software (TreeStar).

Statistical analysis: We performed analysis of variance (ANOVA) and 2-sample t test for statistical analysis. We determined significant difference in survival studies using Kaplan-Meier plots and the Mantel-Cox rank test.

Example 2

In Vivo Targeting of B-Cell Lymphoma with CD22-Targeting Liposomes

Figure 1B:
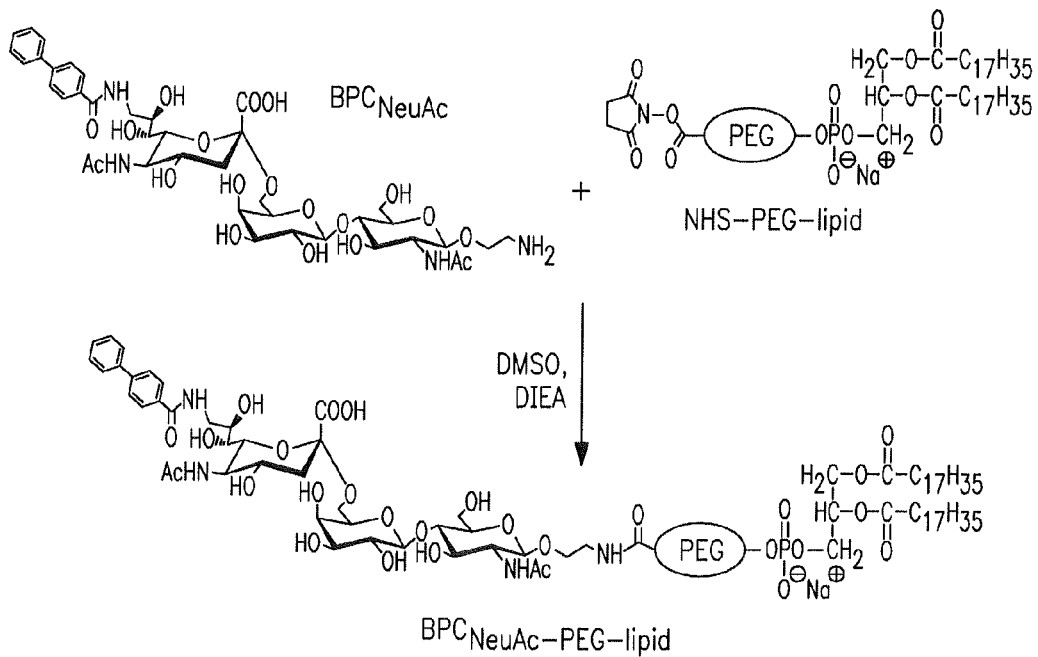

CD22-targeting liposomes are bound to and internalized by CD22-expressing cells: To prepare CD22-targeting liposomes, we coupled a high-affinity glycan ligand of CD22, biphenylcarboxyl-NeuAcα2-6Galβ1-4GlcNAc ($^{BPC}$NeuAc or 6'-$^{BPC}$NeuAc), to a commercially available NHS-activated pegylated lipid, and the corresponding $^{BPC}$NeuAc-pegylated lipid was then incorporated into a liposomal doxorubicin formulation (FIG. 1A-B) analogous to that in current clinical use. Fluorescently labeled $^{BPC}$NeuAc liposomes bound robustly to CD22-expressing but not wild-type CHO cells, whereas the nontargeted "naked" liposomes exhibited no binding to either (FIG. 2A). Fluorescence microscopy shows staining of CD22-expressing cells only by $^{BPC}$NeuAc liposomes (FIG. 2B), with diffuse staining of the cell surface, and punctate staining consistent with internalization by endocytosis, as evidenced by costaining with markers of early endosomes (anti-EEA1; FIG. 2C) and lysosomes (LysoTracker).

$^{BPC}$NeuAc liposomes deliver cytotoxic cargo to Daudi human B lymphoma cells: The human Burkitt lymphoma Daudi B-cell line, commonly used for evaluating drugs for treatment of B-cell lymphomas, was next used to test the B-cell targeting of the $^{BPC}$NeuAc liposomes. Binding assays were conducted at 37° C. in 100% serum to mimic in vivo conditions. Liposomes without targeting ligands exhibit no detectable binding to Daudi cells, whereas liposomes with $^{BPC}$NeuAc lipids show increased binding to the cells as the amount of ligand is increased from 0.8 to 5% (FIG. 2D). Binding and uptake of $^{BPC}$NeuAc liposomes to Daudi cells is rapid, saturable, and competitively inhibited by the presence of free glycan ligands of CD22 (FIG. 2E-F). When dox (adriamycin), a standard chemotherapeutic drug, was loaded into liposomes, the nontargeted naked liposomes exhibited a 175-fold reduction in cell killing relative to free dox, representing protection of the cells by encapsulation of the drug. In contrast, $^{BPC}$NeuAc liposomes exhibited a 33-fold higher potency ($IC_{50}$=1.6 µM) in cytotoxicity of Daudi cells (FIG. 2G) than that of the naked liposomes ($IC_{50}$=53 µM), a difference predictive of increased efficacy in vivo.

Pharmacokinetics and Siglec specificity of $^{BPC}$NeuAc liposomes: In preparation for in vivo efficacy studies, the specificity of $^{BPC}$NeuAc liposome binding to Daudi cells was assessed when spiked into an aliquot of mouse whole blood (FIG. 3A top panel). Binding is specific for the Daudi cells (hCD19$^+$), with negligible binding to all murine cells (hCD19$^-$), including murine B cells, because murine CD22 does not recognize the $^{BPC}$NeuAc ligand. In addition, $^{BPC}$NeuAc liposomes injected intravenously 30 minutes after injection of 1×10$^6$ Daudi cells also efficiently bound the hCD19$^+$ Daudi cells in the blood (FIG. 3A bottom panel). These results show $^{BPC}$NeuAc liposomes efficiently target human B lymphoma cells both in vitro and in vivo.

Figure 3F:
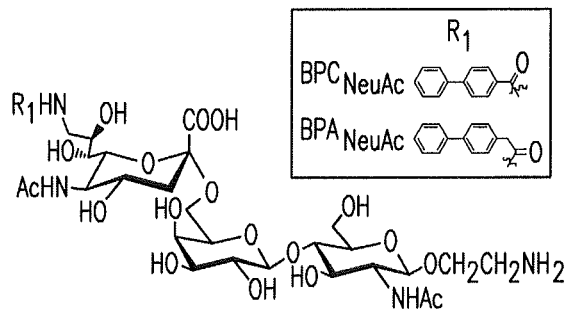
Figure 3F:
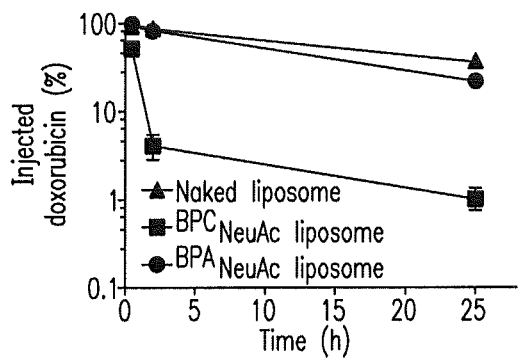
Figure 3G:
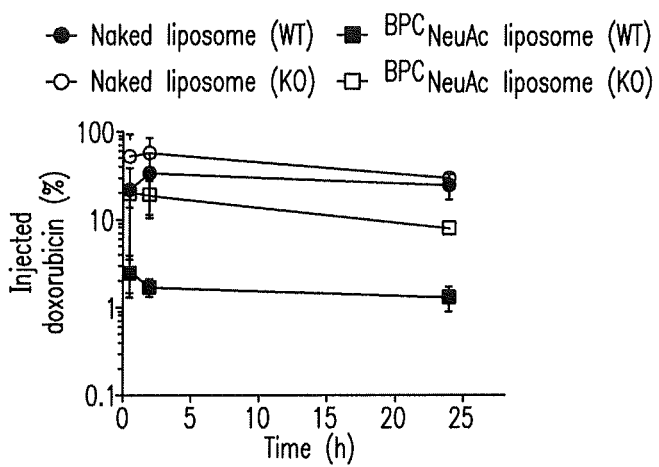

In preliminary pharmacokinetics studies, we observed that the $^{BPC}$NeuAc liposomes showed faster clearance from the blood relative to the naked liposomes in tumor-free animals (FIG. 3B). We deduced that this was likely due to a known cross-reactivity of the $^{BPC}$NeuAc ligand for another Siglec, Sn (Siglec-1). Because Sn is expressed exclusively on tissue macrophages, we repeated the pharmacokinetics in mice depleted of macrophages using liposomal clodronate. This macrophage-specific treatment dramatically reduced clearance to that of naked liposomes (FIG. 3C), demonstrating that clearance was indeed mediated by macrophages. To investigate this further, we tested binding against a panel of cell lines expressing human and murine Siglecs, revealing that the $^{BPC}$NeuAc liposomes did indeed bind to human (but not murine) CD22 (Siglec-2) and murine/human Sn (FIG. 3D). To address the possibility that the sialylated ligand might be abrogating the "stealth" character of the liposomes, leading to nonspecific uptake by macrophages, we prepared liposomes containing a highly related ligand, $^{BPA}$NeuAc, where the BPC substituent was replaced with a 9-N-biphenylacetyl (BPA), which binds poorly to Sn. As expected, the $^{BPA}$NeuAc liposomes exhibited no binding to Sn while retaining binding to hCD22, albeit with reduced affinity (FIG. 3E). These liposomes exhibited reduced clearance equivalent to that of the naked liposomes (FIG. 3F), demonstrating that the ligand does not abrogate the stealth character of the liposomes. To confirm that the macrophage clearance of the $^{BPC}$NeuAc liposomes was indeed mediated by Sn, we conducted pharmacokinetics in Sn-deficient mice, which revealed minimal difference in the clearance rate of the $^{BPC}$NeuAc and naked liposomes (FIG. 3G). Thus, the rapid clearance of the $^{BPC}$NeuAc liposomes is due to a specific and rapid uptake by macrophages mediated predominately by Sn. Although the $^{BPA}$NeuAc liposomes exhibited higher specificity for CD22, their lower avidity reduces their binding to native Daudi cells (FIG. 3E), precluding their use for investigation of efficacy in an in vivo model of human lymphoma. Accordingly, we envisioned the use of $^{BPC}$NeuAc liposomes in a 2-dose protocol, assuming that uptake by macrophages would be blunted after the first dose, in analogy to the use of clodronate that ablated uptake of $^{BPC}$NeuAc liposomes (FIG. 3C).

Figures 4A, 4B:
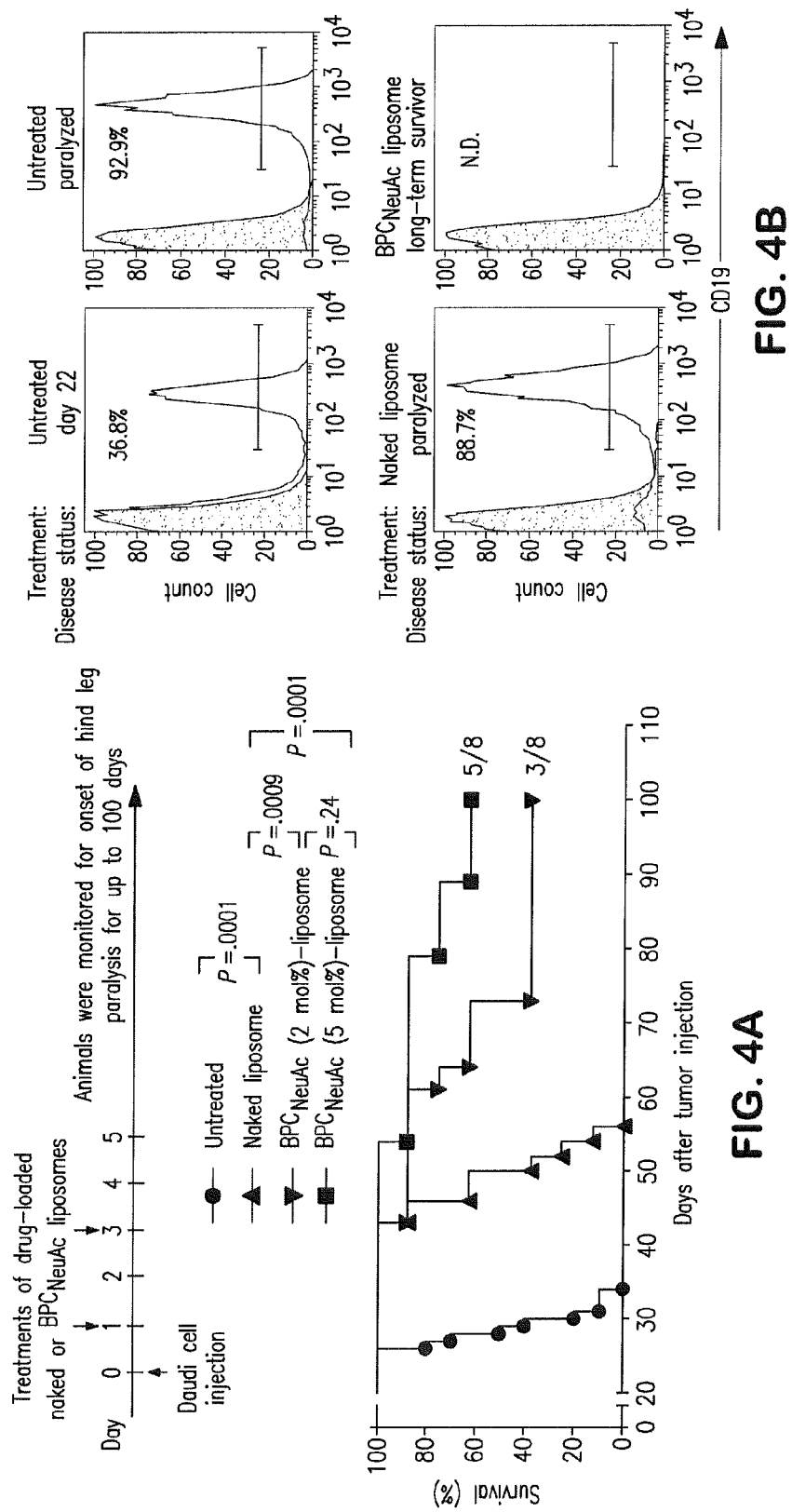
FIGS. 4A-4B show efficacy of CD22-targeting liposomes in a xenograft model of the disseminated Daudi human B lymphoma. (A) Top panel shows timeline for the in vivo efficacy study. Bottom panel: tumor-bearing mice that received PBS (untreated, n=10), dox-loaded naked liposomes (n=8), or BPCNeuAc liposomes (n 8) containing 2% or 5% BPCNeuAc ligands were monitored for the onset of hind-leg paralysis for up to 100 days. Survival rate is presented in a Kaplan-Meier plot with indication of numbers of long-term survivor animals. (B) Estimation of residual Daudi lymphoma cells in the bone marrow. Shown are histograms of bone marrow cells isolated from tumor-bearing mice followed by staining with isotype (solid) or anti-human CD19 (line) antibodies to identify infiltrated Daudi cells. Shown are results from 1 of 3 representative mice that received the indicated treatment. Percentages of lymphoid gated CD19+ Daudi cells in the bone marrow are indicated. N.D. (not detected) refers to less than a 0.4% background observed for an IgG isotype control.

$^{BPC}$NeuAc liposomes prolong life in a murine model of human B-cell lymphoma: The efficacy of dox-loaded CD22-targeting liposomes was evaluated in a standard Daudi lymphoma model in SCID mice. As illustrated by the timeline in FIG. 4A, Daudi cells (5×10$^6$) were injected intravenously and allowed to disseminate for 24 hours, followed by dosing mice on days 1 and 3 with PBS, dox-loaded naked liposomes, or $^{BPC}$NeuAc liposomes (3 mg dox/kg per dose). As anticipated, pharmacokinetics analysis showed that rapid loss of $^{BPC}$NeuAc liposomes from blood after the first dose was significantly attenuated after the second dose. Untreated animals (PBS) had a mean time of survival (MTS) of 28.5 days, whereas the dox-loaded naked liposomes increased the MTS to 50 days. In contrast, liposomes displaying 2% $^{BPC}$NeuAc ligands exhibited a MTS of 73 days, with 3 of 8 long-term survivors being healthy at the end of the study (day 100), and liposomes with 5% ligands demonstrated a MTS greater than 100 days with 5 of 8 long-term survivors. Both treatments with drug-loaded $^{BPC}$NeuAc liposomes comprising 2% or 5% ligands proved significant in improving survival rates compared with the treatment of the nontargeted (naked) liposomal regimen. Follow-up analysis revealed that hCD19+ Daudi cells constituted most bone marrow cells in paralyzed untreated or naked liposome-treated animals. In contrast, residual tumor cells were not detectable above background (Ig isotype control) in the bone marrow of the long-term survivors at day 100, further demonstrating the efficacy of the CD22-targeting liposomal regimen (FIG. 4B; Table 1).

TABLE 1

Detection of residual Daudi tumor cells in the bone marrow of the paralyzed or the long-term survivor mice

| Treatment group | Disease status | N | Murine cells (hCD19−), % | Daudi B cells (hCD19+), % |
|---|---|---|---|---|
| Untreated | 22 d | 3 | 52.4 | 47.6 ± 9.1 |
| Untreated | Paralyzed | 3 | 5.0 | 95.1 ± 3.1 |
| Dox naked liposomes | Paralyzed | 3 | 9.5 | 90.5 ± 3.3 |
| Dox-$^{BPC}$NeuAc (2%) liposomes | Survivor | 3 | 99.7 | ND |
| Dox-$^{BPC}$NeuAc (5%) liposomes | Survivor | 5 | 99.8 | ND |

ND indicates not detectable compared with isotype control (<0.4%).

$^{BPC}$NeuAc liposomes target B cells from blood of patients with lymphoma: We next analyzed the ability of the $^{BPC}$NeuAc liposomes to bind to neoplastic B cells from patients with leukemia/lymphoma. Blood samples were obtained from 4 healthy donors and 30 patients with hairy cell leukemia (HCL), chronic lymphocytic leukemia (CLL), or splenic marginal zone lymphoma (MZL). These are 3 indolent lymphoproliferative disorders, known to express varying levels of CD22 (HCL, high; MZL, moderate; and CLL, low). Although most B cells in CLL and MZL samples are neoplastic cells, in the case of HCL, it is not uncommon to observe the normal and neoplastic B cells segregating into 2 distinct populations upon costaining with anti-CD22 and another B-cell marker (e.g., CD19). When this was observed, neoplastic B cells were distinguished from the normal B cells by staining with anti-CD103 (expressed on most HCL cells and usually present on MZL cells), anti-CD5 (expressed on CLL cells), and anti-κ and anti-λ light chain probes.

All blood samples were assessed for their levels of B-cell expression of CD22 and the binding to the $^{BPC}$NeuAc liposomes. In all cases, control naked liposomes bound no better to the CD19+ B cells than the non-B cells. In contrast, B cells from all patients bound to CD22-targeting liposomes in proportion to their CD22 expression, regardless of their prior treatment history. The CD22-targeting liposomes were confirmed not to cross-react with neutrophils, known to express high levels of CD33 (Siglec-3). B cells from the patients with HCL and MZL bound strongly to the $^{BPC}$NeuAc liposomes, whereas B cells from patients with CLL bound at lower levels. Using mean channel fluorescence (MCF) as a quantitative measure, binding of $^{BPC}$NeuAc liposomes strongly correlated with the expression of CD22, whereas there was no correlation with binding to CD20, which is the target of the anti-CD20 antibody rituximab used in standard treatment of B-cell lymphomas (FIG. 5A).

Despite variation of CD22 expression, malignant B cells from patients with HCL, MZL, and CLL were sensitive to cell killing by the dox-loaded $^{BPC}$NeuAc liposomes in an in vitro assay (FIG. 5B). The assay involves exposure of the peripheral blood leukocytes to the liposomal preparations for 1 hour, followed by incubation of the cells for 5 days in media. Cell viability was assessed using a standard MTT assay. Whereas HCL and MZL were susceptible to both low (10 μM) and high (40 μM) concentrations of the targeted liposomal dox, CLL cells were efficiently killed only by the higher dox concentration. Taken together, the results indicate that while binding of the CD22-targeting liposome to malignant B cells is proportional to CD22 expression on the cell surface, even low levels of expression on CLL cells are sufficient to effect cell killing. Because the targeted liposomes breach the cells by an endocytic mechanism, it is anticipated that the therapeutic benefit will be synergistic with anti-CD20 rituximab and other immune-mediated therapies.

Example 3

Liposomes for Targeting and Delivering Antigens to APCs

This Example describes liposomal nanoparticles bearing glycan ligands of Siglecs for targeting and/or delivering antigens to antigen presenting cells (APCs) including macrophages, dendritic cells and B cells. In these studies, incorporation of antigens into the liposomal targeting compositions allows active targeting of antigen presenting cells, resulting in an immune response with robust activation of T cells or NKT cells depending on the antigen delivered. Specifically, we demonstrated (1) targeting in vitro and in vivo macrophages with antigen that is processed for presentation and activation of CD4+ and CD8+ T cells, (2) targeting in vitro and in vivo macrophages with lipid linked antigen that is processed for presentation and activation of NKT cells, and 3) targeting in vitro dendritic cells with protein antigen that is processed for presentation and activation of T cells.

In these studies, we employed liposomal nanoparticles that display glycan ligands for two Siglecs. One liposomal nanoparticle bears ligands for sialoadhesin (Sn)/Siglec-1 (9-N-biphenylcarboxyl-NeuAcα2-3Galβ1-4GlcNAc) targets macrophages (3'-$^{BPC}$NeuAc liposomes), and the other bears ligands for murine CD22 (9-N-biphenylacetyl-NeuGcα2-6Galβ1-4GlcNAc) targets B cells and murine dendritic cells ($^{BPA}$NeuGc-α2,6-liposomes). We observed that these targeted nanoparticles are bound by and rapidly endocytosed by the cells bearing the respective Siglec. Dendritic cells, macrophages and B cells are known as professional antigen presenting cells of the immune system. Incorporating an antigen into the Siglec ligand decorated liposomes resulted in the targeted delivery of the antigen to the immune cell bearing the respective Siglec. As detailed below, results obtained from these studies are shown in FIGS. 6-20.

Figure 6:
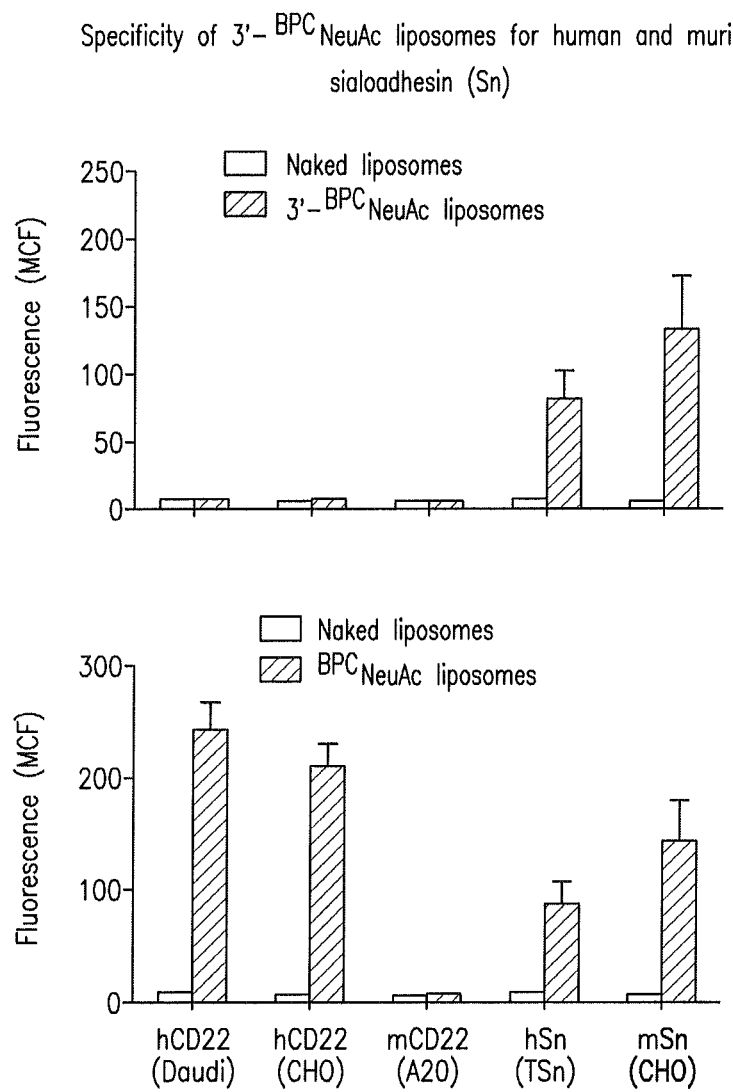
FIG. 6 shows specificity of 3'-$^{BPC}$NeuAc-liposomes for human and murine sialoadhesin (Sn).

We first examined targeting specificity of the liposomes used in the studies. As shown in FIG. 6, we observed that liposomes displaying 3'-$^{BPC}$NeuAc ligands target cells that express sialoadhesin (Sn, Siglec-1). Shown in the top panel of the figure is FACS analysis for binding of naked or 3'-$^{BPC}$NeuAc liposomes to cell lines that express human or murine Sn or CD22 (Siglec-2). Daudi (expressing hCD22), A20 (expressing mCD22), TSn (expressing hSn) and CHO (expressing hCD22 or mSn) cell lines were incubated with fluorescently labeled naked or 3'-$^{BPC}$NeuAc liposomes at 37° C. for 1 hr prior to FACS analysis. Binding of liposomes is expressed as mean channel fluorescence (MCF)±s.d. (n=3). Naked liposomes were formulated with pegylated-lipids without glycan ligands. The bottom panel of the figure shows that liposomes formulated with the first generation CD22 ligand (6'-$^{BPC}$NeuAc) as described above has cross binding to both human CD22 and Sn.

Figure 7:
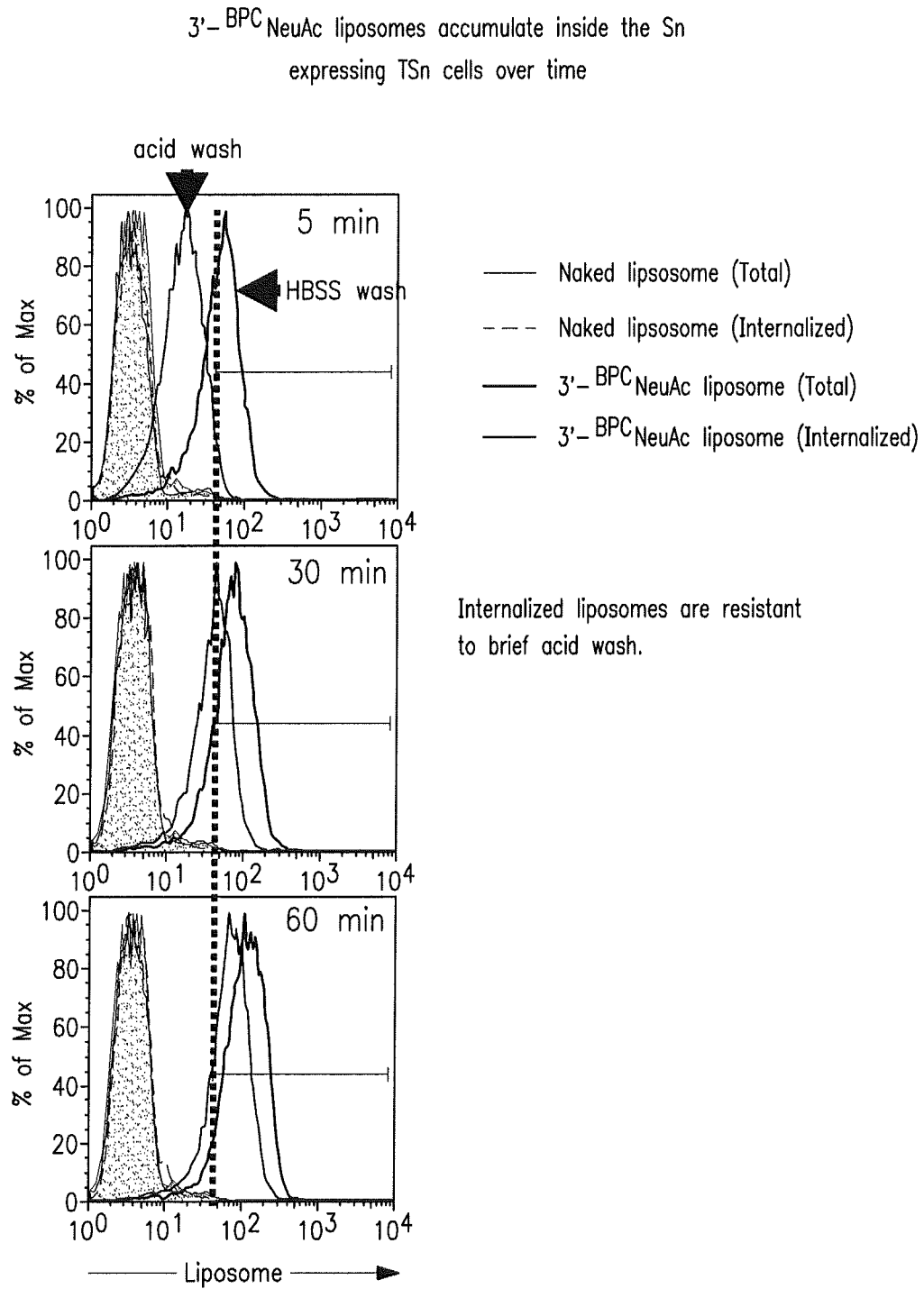
FIG. 7 shows that 3'-$^{BPC}$NeuAc-liposomes accumulate inside the Sn expressing TSn cells over time.

We additional observed that liposomes displaying 3'-$^{BPC}$-NeuAc ligands, but not naked liposomes, are internalized by Sn-expressing cells (FIG. 7). TSn cells that express hSn were incubated with naked or 3'-$^{BPC}$NeuAc liposomes for 5, 30 or 60 min at 37° C. Cells were washed with acid (pH 3.3, to remove surface binding) or HBSS (HEPES buffered salt solution) followed by FACS analysis to determine levels of internalized liposomes or total liposome binding, respectively. Liposomes without targeting ligands exhibit no detectable binding to TSn, while 3'-$^{BPC}$NeuAc liposomes exhibit rapid total binding (thick and bold solid line) and the increased internalization (thick solid line) by TSn cells. Cells treated with medium (filled grey) were used as a negative control. In separate studies, it was observed that Sn-targeted liposomes, but not anti-Sn antibodies, accumulated in cells. Specifically, Sn-expressing THP-1 cells were incubated with liposomes (3'-BPCNeuAc) or antibodies (anti-Sn Ab or isotype control Ab) at 37° C. for 5, 20 or 90 min. Stained cells were washed and analyzed by flow cytometry. The results indicate that Sn-targeted liposomes but not anti-Sn antibodies accumulate in cells.

Additional studies indicate that 3'-$^{BPC}$NeuAc liposomes are taken up by Sn-expressing cells and are co-localized with lysosomes. CHO cells expressing Sn were compared for binding to the fluorescent 3'-$^{BPC}$NeuAc liposomes or naked liposomes. Sn was detected with anti-mSn and the nuclei were visualized by staining with DAPI. TSn cells were co-stained with 3'-$^{BPC}$NeuAc liposomes and anti-lysosome. Punctate staining suggests internalization of 3'-$^{BPC}$NeuAc-liposomes. Merging shows co-localization of 3'-$^{BPC}$NeuAc liposomes with lysosomes.

Figure 8:
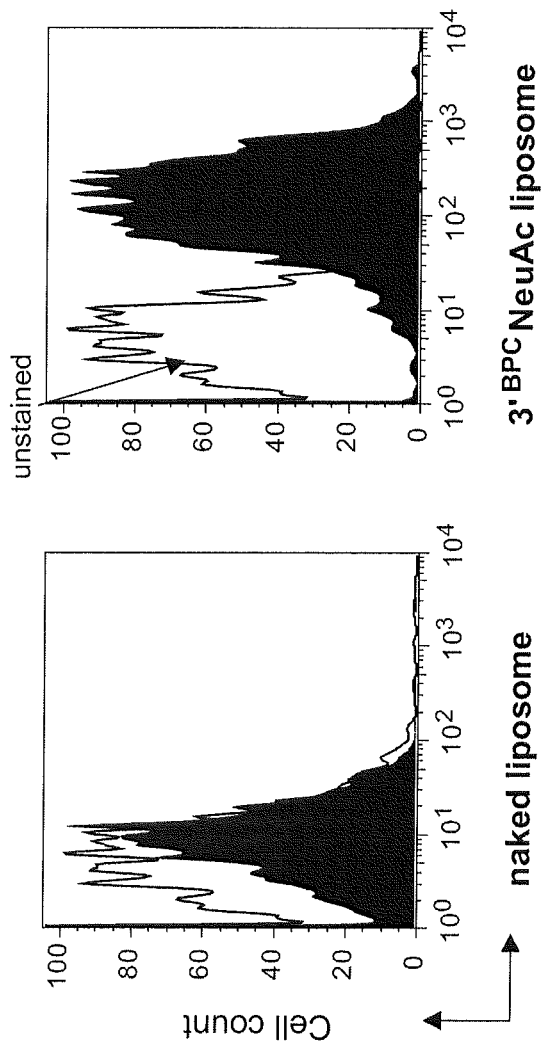
FIG. 8 shows that liposomes bind to macrophages in lymph node.

We also ascertained that Sn-targeted liposomes, but not naked liposomes, bind to tissue macrophages in lymph nodes (FIG. 8). Sn was reported being expressed on the surface of tissue macrophages. In this study, we tested if 3'-$^{BPC}$NeuAc liposomes bind to tissue macrophages. Fluorescent naked (FIG. 8, left panel) or 3'-$^{BPC}$NeuAc liposomes (FIG. 8, right panel) were incubated with the freshly harvested mouse lymph node cells at 37° C. for 1 hr following co-staining with anti-CD11b prior to FACS analysis. The histograms shown were based on gating CD11b+ cells (macrophages) in lymph nodes. Cells treated with medium alone (filled black) were used as a negative control.

Figure 9:
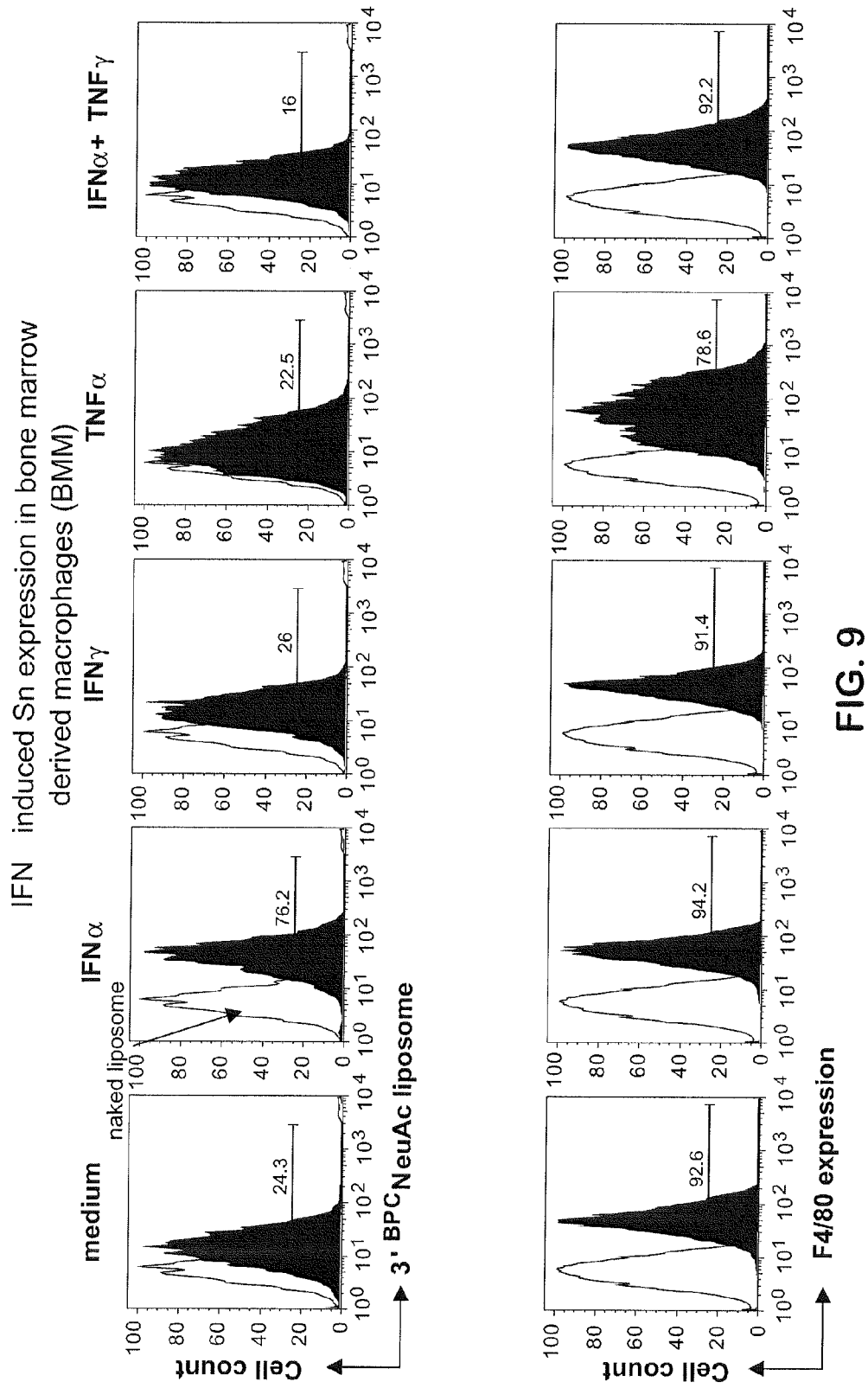
FIG. 9 shows that IFNα induced Sn expression in bone marrow derived macrophages (BMM).

We further examined IFNα-induced Sn expression in bone marrow derived macrophages (BMM). In this study, mouse bone marrow cells were in vitro cultured for 7 days with presence of the indicated cytokine. As shown in the top panel of FIG. 9, cells were compared for binding to the fluorescent 3'-$^{BCP}$NeuAc liposomes (filled black) and naked liposomes (unfilled graph). BMM treated with IFNα show an increased binding to 3'-$^{BPC}$NeuAc liposomes comparing to other cytokine treatments. At the end of the 7-day culture, bone marrow cells exhibit macrophage phenotype (F4/80+) regardless of treatment (FIG. 9, bottom panel).

Figure 10:
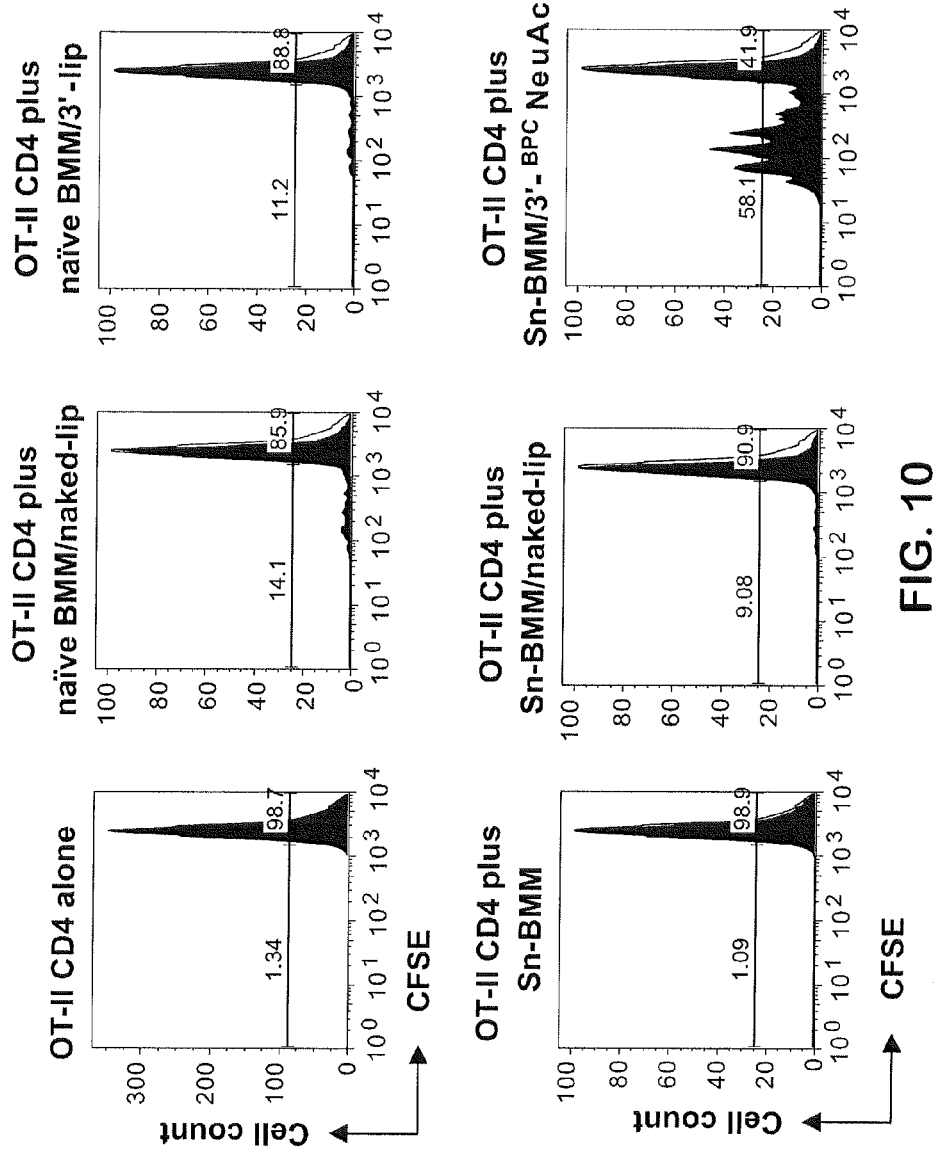
FIG. 10 shows that OT-II CD4$^+$ T cell proliferation is induced by 3'-$^{BPC}$NeuAc liposome/OVA treated IFNα-activated BMM.

We then tested targeted delivery of antigens by the liposome composition to antigen presenting cells. First, as shown in FIG. 10, we observed that Sn-targeted liposomes, but not naked liposomes, deliver a protein antigen (ovalbumin, OVA) to macrophages in vitro, resulting in activating CD4+ T cells. CD4+ T cells purified from OT-II transgenic mice (mice carrying a transgenic CD4 TCR specific for a MHC class II-restricted OVA peptide) were CFSE labeled and were incubated with BM-derived macrophages that have been treated with naked or Sn-targeted liposomes carrying OVA antigens. After 72 hr incubation in vitro, T cells were analyzed for CFSE dilution. In the figure, "Sn-BMM" represents the BM-derived macrophages that were stimulated using IFNα in order to induce Sn expression. The treatment combinations and their effect on OVA CD4+ T cell activation/proliferation are summarized in Table 2 below.

TABLE 2

T cell activation by targeting OVA to macrophage with 3'-$^{BPC}$ NeuAc liposome

| | BM-derived macrophages | Liposomal OVA | OVA T cell proliferation |
|---|---|---|---|
| 1 | — | — | − |
| 2 | Naïve | Naked liposome | +/− |
| 3 | Naïve | 3'$^{BPC}$NeuAc liposome | +/− |
| 4 | Sn-expressing macrophages | — | − |
| 5 | Sn-expressing macrophages | Naked liposome | +/− |
| 6 | Sn-expressing macrophages | 3'$^{BPC}$NeuAc liposome | +++ |

These in vitro results indicate that the Sn-targeted liposomes could deliver an antigen to tissue macrophages (Sn+) such that the macrophages could serve as antigen presenting cells to present antigen to and activate T cells.

Figure 11:
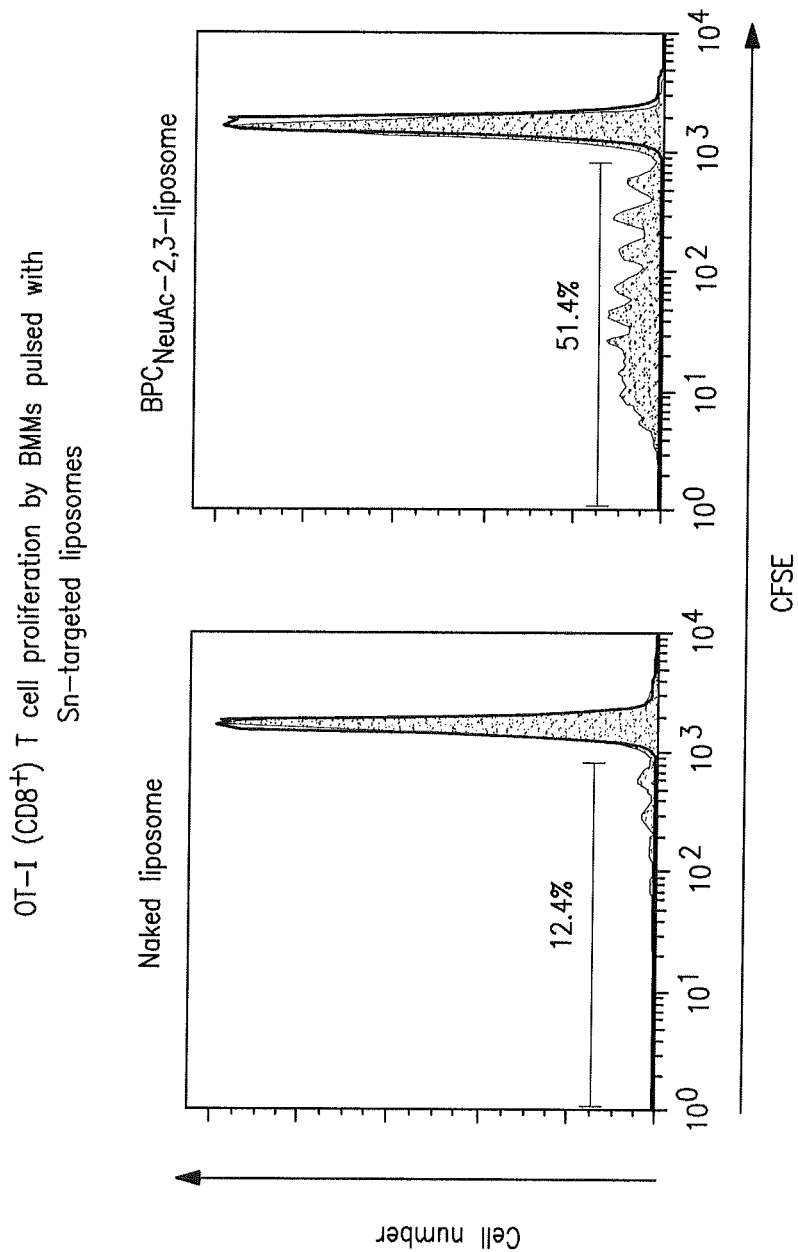
FIG. 11 shows OT-I (CD8$^+$) T cell proliferation induced by BMMs pulsed with Sn-targeting liposomes.

In addition to CD4+ T cells, we also examined the effect of Sn-liposome targeted delivery of OVA to macrophage on CD8+ T cell proliferation. As illustrated in FIG. 11, CD8+ T cells purified from OT-I transgenic mice (mice carrying a transgenic CD8 TCR for a MHC class I-restricted OVA peptide) were CFSE labeled. The cells were incubated with BM-derived macrophages that have been treated with naked or Sn-targeted liposomes carrying OVA antigens. After 4 day incubation in vitro, CFSE dilution of T cells were analyzed by flow cytometry. The results indicate that antigen presenting cells targeted by Sn-targeting liposomes bearing OVA antigens were similarly able to induce proliferation of CD8+ T cells.

Figure 12:
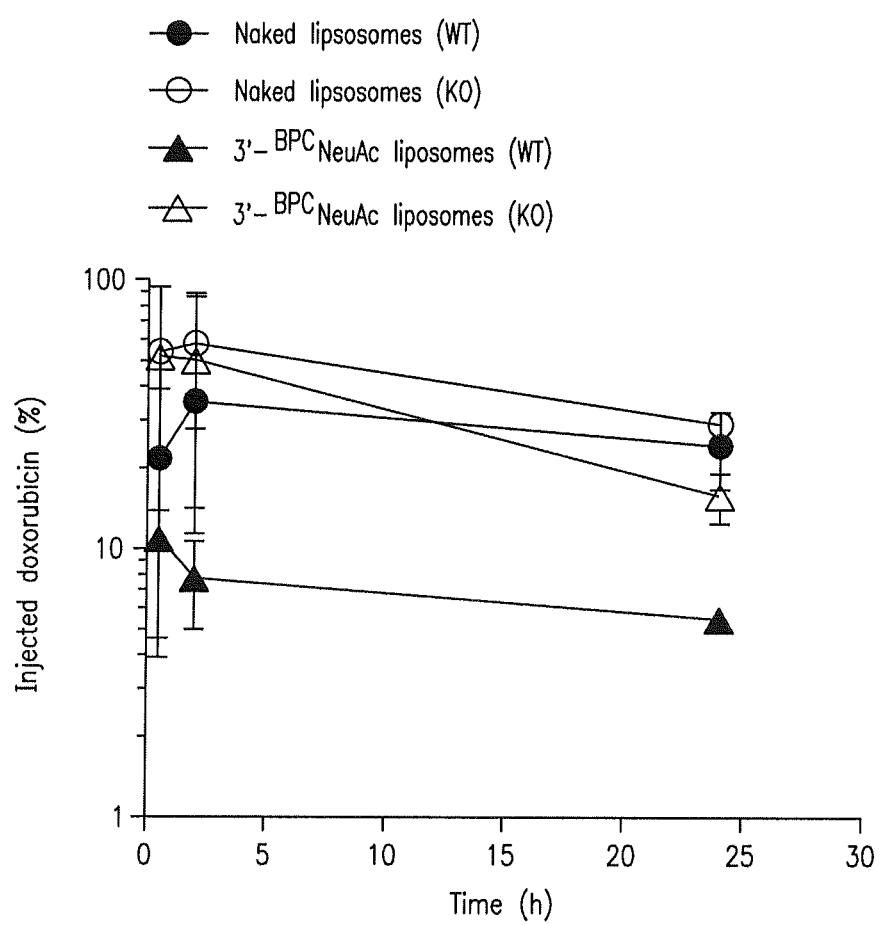
FIG. 12 shows that 3'-$^{BPC}$NeuAc liposomes are rapidly cleared in wild-type animals but not in Sn-knockout animals.

We also found that 3'-$^{BPC}$NeuAc liposomes are cleared faster in wild-type animals but not in Sn-knockout animals (FIG. 12). In FIG. 12, wild type (filled symbols) C57BL/6 and Sn-knockout (KO) (open symbols) mice (3 mice per group) were i.v. injected with the naked (circles) or 3'-$^{BPC}$NeuAc (triangles) liposomes that encapsulate equal amount of doxorubicin. Plasma samples were collected at indicated time points and were analyzed for the remaining doxorubicin concentration in the plasma comparing to the initial injection dose.

Figure 13:
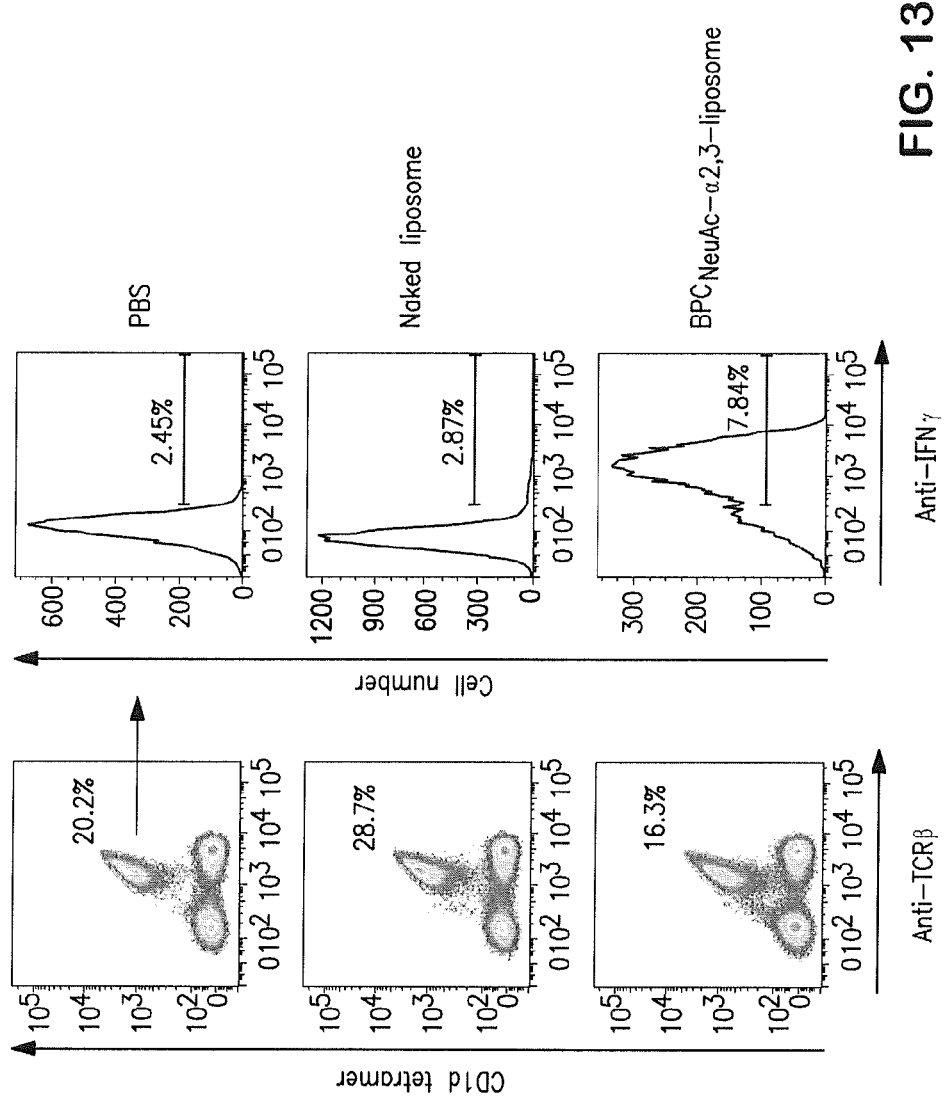
FIG. 13 shows that Sn-targeting liposomes deliver the antigen (α-gal-ceramide) to macrophages that present and activate NKT cells in vivo.

Moreover, we studied the effect of Sn-liposome targeted antigen delivery on NKT cells in vivo. In this study, C57BL/6 mice were i.v. injected with the naked and 3'-$^{BPC}$NeuAc liposomes that encapsulate 40 ng of α-gal-ceramide or vehicle alone (PBS). After 90 min, intrahepatic lymphocytes were isolated and stained with anti-TCRb and α-gal-ceramide loaded CD1d tetramer to identify NKT cells. Stained cells were fixed, permeabilized, and stained with anti-IFNγ. The cells were then washed and analyzed by flow cytometry. As shown in FIG. 13, the results indicate that upon Sn-liposomes mediated deliver of the antigen, the macrophages were able to present the antigen and activate NKT cells in vivo.

Figure 14:
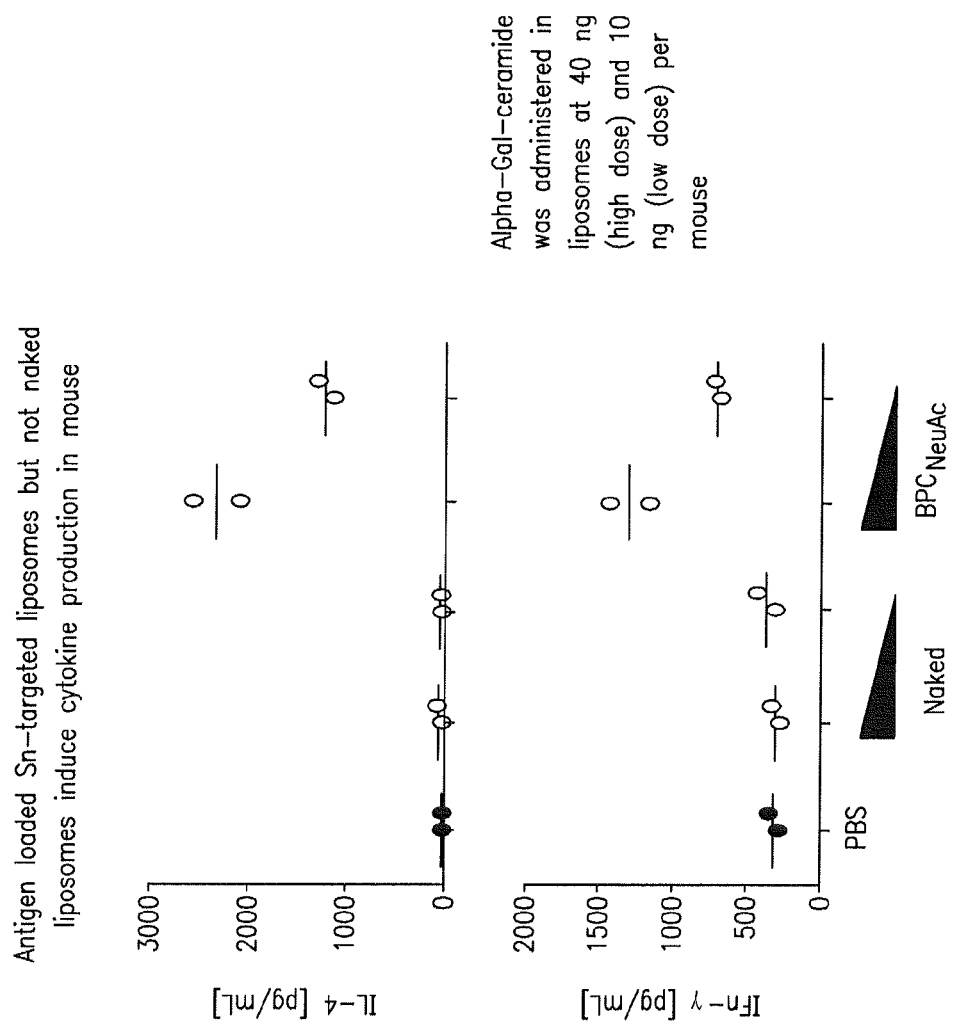
FIG. 14 shows that antigen loaded Sn-targeting liposomes but not naked liposomes induce cytokine production in mouse.

We also analyzed cytokine production in mice treated with the antigen-bearing Sn-liposomes. C57BL/6 mice were i.v. injected with the naked and 3'-$^{BPC}$NeuAc liposomes that encapsulate 40 ng and 10 ng of α-gal-ceramide and vehicle alone (PBS). After 90 min, the blood was harvested and the concentration of IL-4 and IFNγ in the serum of injected mice was determined by ELISA. As shown in FIG. 14, antigen loaded Sn-liposomes, but not naked liposomes, induced cytokine production in mouse.

Figure 15:
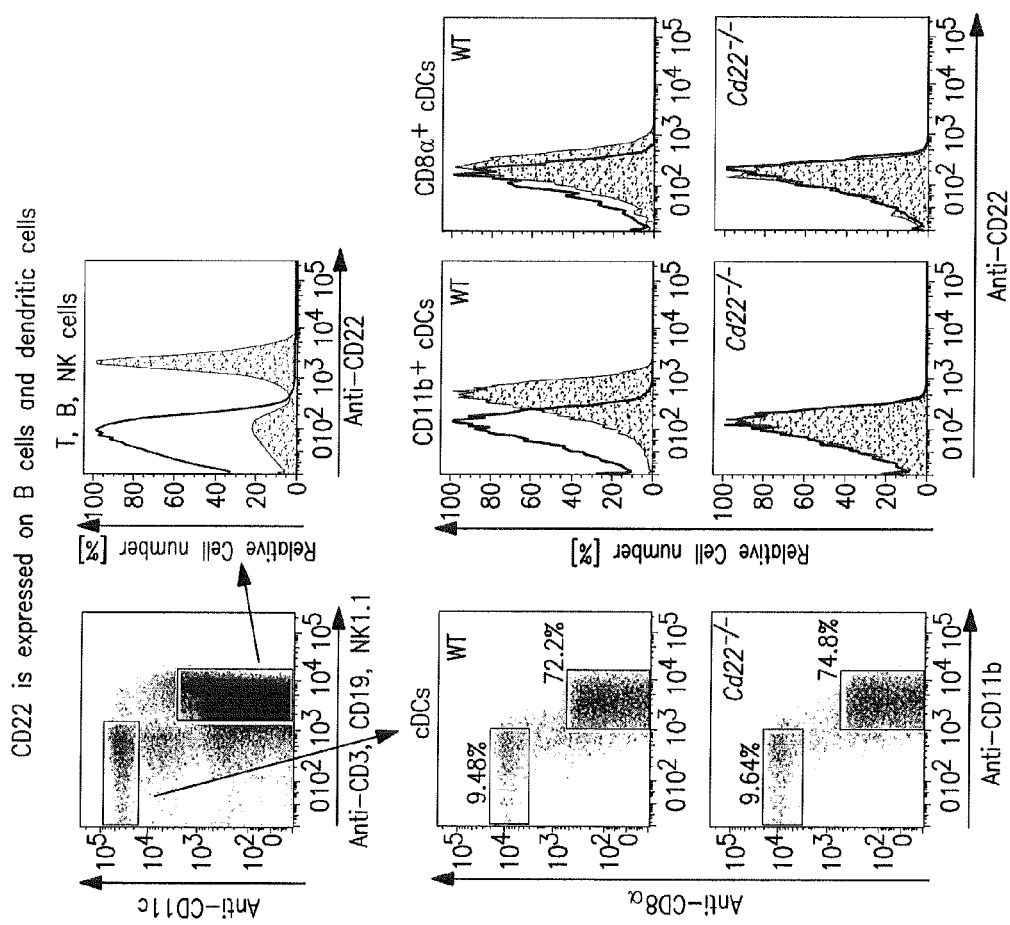
FIG. 15 shows that CD22 is expressed on B cells and dendritic cells.

Other than macrophage expressing Siglec-1 (Sn), we also examined whether other antigen presenting cells such as B cells and dendritic cells also express Siglec (FIG. 15). Splenocytes from wild type (WT) C57BL/6 and Cd22$^{-/-}$ mouse were stained with anti-CD3, CD19, NK1.1, CD11b, CD11c, CD8a, and CD22 or isotype matched control Ab. Anti-CD3, CD19, and NK1.1 mAbs were used to exclude T, B, and NK cells. Conventional dendritic cells (lineage$^-$CD11c$^{high}$) were plotted on CD11b and CD8a staining to identify DC subsets. CD22 expression in each population was checked. As shown in the figure, the results indicate that CD22 is expressed on B cells and dendritic cells.

Upon ascertaining Siglec expression on B cell and dendritic cells, we then tested targeting of these cells with liposomes. Unlike the Sn-targeting liposome (3'-$^{BPC}$NeuAc liposome), the liposomes used in this study for targeting CD22 ($^{BPA}$NeuGc-liposomes) bear a different glycan ligand. Splenocytes from WT and Cd22$^{-/-}$ mouse were stained with naked or $^{BPA}$NeuGc-α2,6-liposomes and anti-CD11b, CD11c, and CD19 Abs to identify DCs and B cells. Liposome positive population was plotted on CD19 and CD11c staining. 98.2% of liposome+ cells were B cells and 0.9% was CD11b$^+$DCs. The liposome binding to DCs was abrogated in Cd22$^{-/-}$ DCs, showing $^{BPA}$NeuGc-α2,6-liposomes target DCs through CD22. The results indicate that $^{BPA}$NeuGc-α2,6-liposomes specifically targeted to the CD22-expressing B cells and dendritic cells.

With the CD22 targeting ability of the $^{BPA}$NeuGc-α2,6-liposomes, we then examined activity of the liposome for targeted delivery of OVA antigens to CD22-expressing antigen presenting cells (FIG. 16). CD4+ T cells purified from OT-II transgenic mice were CFSE labeled and were incubated with BM-derived dendritic cells that have been treated with naked or CD22-targeting liposomes ($^{BPA}$NeuGc-α2,6-liposome) carrying OVA antigens. After 4 day incubation in vitro, CFSE dilution of T cells were analyzed by flow cytometry. As indicated in the figure, targeted delivery of the antigen to the dendritic cells via the $^{BPA}$NeuGc-α2,6-liposome was able to induce proliferation of the OT-II T cells.

The invention thus has been disclosed broadly and illustrated in reference to representative embodiments described above. It is understood that various modifications can be made to the present invention without departing from the spirit and scope thereof. It is further noted that all publications, patents and patent applications cited herein are hereby expressly incorporated by reference in their entirety and for all purposes as if each is individually so denoted. Definitions that are contained in text incorporated by reference are excluded to the extent that they contradict definitions in this disclosure.

What is claimed is:

1. A method for activating an immune response in T cells to a polypeptide or glycolipid antigen, comprising
    (a) providing a liposome targeting compound comprising a liposome and a glycan ligand for a Siglec on a human or mouse macrophage or dendritic cell, wherein the glycan ligand is displayed on the liposome and the polypeptide or glycolipid antigen is incorporated into the liposome; and
    (b) contacting the liposome targeting compound with the macrophage or dendritic cell;
thereby activating an immune response in T cells to the antigen.

2. The method of claim 1, wherein the activated immune response in T cells is activation of CD4$^+$ and CD8$^+$ T cells.

3. The method of claim 1, wherein the glycolipid antigen is an activator of natural killer T (NKT) cells, and wherein the activated immune response in T cells is activation of NKT cells.

4. The method of claim 1, wherein the liposome targeting compound is contacted with the macrophage or dendritic cell in vitro.

5. The method of claim 1, wherein the liposome targeting compound is administered to a subject and contacted with the macrophage or dendritic cell inside the body of the subject.

6. The method of claim 1, wherein the Siglec is sialoadhesin.

7. The method of claim 1, wherein the glycan ligand is 9-N-biphenylcarboxyl-NeuAcα2-3Galβ1-4GlcNAc (3'-$^{BPC}$NeuAc).

* * * * *